(12) United States Patent
Robb et al.

(10) Patent No.: US 10,613,102 B2
(45) Date of Patent: Apr. 7, 2020

(54) RED BLOOD CELL DETECTION

(71) Applicant: QBD (QS-IP) Limited, St Helier (GB)

(72) Inventors: Janine Scott Robb, Midlothian (GB); Andrew Gordon Robb, Midlothian (GB); David Cooper Robson, Midlothian (GB)

(73) Assignee: QBD (QS-IP) Limited, Jersey (GB)

( * ) Notice: Subject to any disclaimer, the term of this patent is extended or adjusted under 35 U.S.C. 154(b) by 86 days.

(21) Appl. No.: 15/119,291

(22) PCT Filed: Feb. 20, 2015

(86) PCT No.: PCT/GB2015/050502
§ 371 (c)(1),
(2) Date: Aug. 16, 2016

(87) PCT Pub. No.: WO2015/124947
PCT Pub. Date: Aug. 27, 2015

(65) Prior Publication Data
US 2017/0059591 A1 Mar. 2, 2017

(30) Foreign Application Priority Data
Feb. 21, 2014 (GB) .................................. 1403115.7

(51) Int. Cl.
*G01N 33/80* (2006.01)
*G01N 33/555* (2006.01)

(52) U.S. Cl.
CPC ........... *G01N 33/80* (2013.01); *G01N 33/555* (2013.01)

(58) Field of Classification Search
None
See application file for complete search history.

(56) References Cited

U.S. PATENT DOCUMENTS

| | | | |
|---|---|---|---|
| 5,086,002 | A | 2/1992 | Hillyard et al. |
| 5,101,017 | A | 3/1992 | Rubinstein et al. |
| 2005/0260292 | A1 | 11/2005 | Yang |
| 2007/0042499 | A1 | 2/2007 | Schwind et al. |
| 2012/0202225 | A1 | 8/2012 | Knutson et al. |

FOREIGN PATENT DOCUMENTS

| | | |
|---|---|---|
| JP | 2002250729 | 9/2002 |
| JP | 2009531694 | 9/2009 |
| JP | 2010271282 | 12/2010 |
| WO | WO 90/00614 | 1/1990 |
| WO | WO 2003/021275 A1 | 3/2003 |
| WO | WO 2006/100477 A1 | 9/2006 |
| WO | 2007/110605 | 10/2007 |
| WO | WO 2008/035047 A1 | 3/2008 |
| WO | WO 2012/010666 A1 | 1/2012 |

OTHER PUBLICATIONS

Morelati et al. (Blood Transfusion 2007 vol. 5, p. 58-65). (Year: 2007).*
Sharon et al. (Cytometry 1991 12:545-549). (Year: 1991).*
Looney et al. "Evaluation of a Protein Microarray Method for Immuno-Typing Erythrocytes in Whole Blood", *Journal of Immunoassay & Immunochemistry*, 29: 197-209, 2008.
Bianchi et al. "Erythroid-Specific Antibodies Enhance Detection of Fetal Nucleated Erythrocytes in Maternal Blood", *Prenatal Diagnosis*, vol. 13, (1993), pp. 293-300.
Blancher et al. "Cross-Reactivity of Antibodies to Human and Primate Red Cell Antigens", *Transfusion Medicine Reviews*, vol. 14, No. 2, Apr. 2000: pp. 161-179.
Campbell et al. "Cell Interaction Microarray for Blood Phenotyping", *Anal. Chem*, 2006, 78, pp. 1930-1938.
Daniels et al. "Blood Group Terminology 2004: From the International Society of Blood Transfusion Committee on Terminology for Red Cell Surface Antigens", Vox Sanguinis, (2004) 87, pp. 304-316.
Telen et al. "Relationship of the Human Erythrocyte $Wr^b$ Antigen to an Interaction Between Glycophorin A and Band 3", *Blood*, vol. 76, No. 4, 1990, pp. 842-848.
PCT International Search Report dated Apr. 23, 2015 for International Application No. PCT/GB2015/050502.
PCT Written Opinion dated Apr. 23, 2015 for International Application No. PCT/GB2015/050502.
Office Action, Japanese Patent Application No. 2016-553606, dated Dec. 13. 2018, 5 pages.

* cited by examiner

*Primary Examiner* — Changhwa J Cheu
(74) *Attorney, Agent, or Firm* — Myers Bigel, P.A.

(57) ABSTRACT

The present invention is based on the finding that red blood cell antigens can be exploited as a means to detect red blood cells/erythrocytes. Specifically, by identifying red blood cell antigens which are expressed by substantially all red blood cell types, it is possible to provide a method which achieves the reliable detection of red blood cells.

24 Claims, 13 Drawing Sheets

RED BLOOD CELL DETECTION

RELATED APPLICATIONS

This application is a 35 U.S.C. § 371 national phase entry of PCT Application PCT/GB2015/050502, filed Feb. 20, 2015, and published in English on Aug. 27, 2015, as International Publication No. WO 2015/124947 A1, which claims the priority to United Kingdom Application No. 1403115.7, filed Feb. 21, 2014, the disclosure of each of which is incorporated herein by reference in its entirety.

FIELD OF THE INVENTION

The present invention provides methods for detecting red blood cells. The methods of this invention may be used as the basis of control tests for assays. As such, the invention further provides assays which exploit the methods of this invention

BACKGROUND OF THE INVENTION

In any type of assay it is standard accepted practice to include controls which the operator can use to confirm the correct functioning of not only the assay system as a whole but also the correct/proper addition and/or functioning of various reagents, samples and/or equipment. Depending on their function, controls for use in assays, including immunological assays, may be referred to as positive or negative controls.

A number of assays require the addition of red blood cells; these assays include, for example, assays for the blood typing of red blood cell samples as performed routinely in blood donation testing centers and transfusion laboratories worldwide. Tests of this type include ABO and RhD grouping; comprehensive blood type testing may include (but is not limited to) the detection of Rh, Kell, Duffy, MNS and/or Kidd antigens.

Blood typing testing may be carried out as an agglutination test in a test tube. More recently tests of this type have been carried out using solid-phase microplate and column agglutination technologies (aka Gel, CAT). Current state-of-the-art includes commercially available systems such as Beckman Coulter PK7300, Immucor Capture-R, and Bio-Rad ID-System and Ortho Clinical Diagnostics BioVue and ID-MTS systems, and although many other variations are now available, they are very similar in principle to the systems mentioned above.

Assays such as those described above rely on the successful addition of red blood cells. In most cases, the volume and quantity of the consumables/samples is large enough that the successful addition of samples and reagents (such as blood/red blood cells) can be recorded by simple observation. In the case of the addition of red blood cells to assays, their shape, form, density and colour makes them easily detectable. Some systems may use haemagglutination as the end point read out (interpreted by for example photographic technology and software) and the addition of red blood cells is easy to determine not least because the volumes and quantities of consumables (samples and the like) is large enough to permit easy visual detection of red blood cells but also because the haemagglutination process in itself provides evidence of red blood cell addition.

However, miniaturisation of assays presents a need for methods of detecting red blood cells which do not rely (solely) on visual identification. However, any method must respect the diversity of antigens expressed by red blood cells. In humans, red blood cells from persons with different genetic backgrounds and/or from different geographic locales, may express different antigen profiles. As such, any method which is to be exploited as a means to detect red blood cells and/or serve as a control test to confirm the addition of red blood cells, must reliably detect red blood cells of any type.

The presence of antigens (including blood group antigens) on the surface of red blood cells forms the basis of many immunological tests including, for example blood typing assays which may use non-agglutination protein microarrays, in which an immobilised antibody binds to an antigen on the surface of the red blood cells, and the presence of red blood cells so immobilised is detected (J S Robb et al 2006). Antibody microarray technology can also be used to phenotype red blood cells by detecting complex mixtures of antigens on cell surfaces (C. J. Campbell et al 2006). The antigens expressed by red blood cells are both sugar antigens, which tend to be well presented and easily accessible, and protein peptide antigens, which are epitopes of transmembrane or membrane linked proteins and therefore buried and held more closely to the cell surface, and these were successfully differentiated using the correct choice of antibodies.

With the advent of new miniaturised technologies, such as microarrays, surface plasmon resonance, and any other forms of assay/method and/or system which require the use or addition of red blood cells, it is desirable to provide a test or means which can reliably, repeatedly and consistently detect red blood cells of all types. In particular, it is desirable to provide red blood cell detection methods suitable for use in methods and assays/systems which do not (or cannot) use visual detection methods to detect red blood cells. Moreover, it is advantageous to provide a control test which can reliably, consistently and repeatedly report the addition of red blood cells to an assay or assay system.

SUMMARY OF THE INVENTION

The present invention is based on the finding that red blood cell antigens can be exploited as a means to detect red blood cells (sometimes referred to as erythrocytes: references to "red blood cell" in this invention encompass erythrocytes). Specifically, by identifying red blood cell antigens which are expressed by substantially all red blood cell types, it is possible to provide a method which achieves the reliable detection of red blood cells.

Thus, the present invention provides a method of detecting red blood cells in a sample, said method comprising probing a sample for red blood cells which express one or more antigens selected from the group consisting of:
(i) En$^a$;
(ii) Ge:2;
(iii) Ge:3;
(iv) GPA;
(v) GPB;
(vi) H;
(vii) Rh29; and
(viii) Wr$^b$.

The invention further provides a method of detecting red blood cells in a sample, said method comprising contacting the sample with one or more binding agents capable of binding one or more red blood cell antigens selected from the group consisting of:
(i) En$^a$;
(ii) Ge:2;
(iii) Ge:3;

(iv) GPA;
(v) GPB;
(vi) H;
(vii) Rh29; and
(viii) Wr$^b$;

wherein detection of red blood cells bound to the binding agents indicates that the sample contained red blood cells.

Additionally, and in a further aspect, the invention provides one or more binding agents capable of binding one or more antigens selected from the group consisting of:
(i) En$^a$;
(ii) Ge:2;
(iii) Ge:3;
(iv) GPA;
(v) GPB;
(vi) H;
(vii) Rh29; and
(viii) Wr$^b$;

for use in a method of detecting red blood cells and/or for use in an assay (including an immunological assay) or (immunological) assay system.

The invention further provides the use of one or more binding agents capable of binding one or more antigens selected from the group consisting of:
(i) En$^a$;
(ii) Ge:2;
(iii) Ge:3;
(iv) GPA;
(v) GPB;
(vi) H;
(vii) Rh29; and
(viii) Wr$^b$;

in a method of detecting red blood cells and/or for use in an assay (including an immunological assay) or (immunological) assay system.

It should be noted that this invention may exploit a binding agent capable of binding both the GPA and GPB antigens.

For example, the one or more binding agents capable of binding one or more antigens selected from the group consisting of:
(i) En$^a$;
(ii) Ge:2;
(iii) Ge:3;
(iv) GPA;
(v) GPB;
(vi) H;
(vii) Rh29; and
(viii) Wr$^b$;

may find application in control tests or methods for confirming the addition of red blood cells to an assay (for example an immunological assay) or an (immunological) assay system.

For convenience, the red blood cell antigens listed above as (i)-(viii) shall be referred to hereinafter as "antigens (i)-(viii)".

A sample for use in the methods of this invention may be contacted with one or more agents capable of binding red blood cell antigens under conditions which permit binding between the binding agents and any red blood cells present in the sample. Such conditions may include one or more pre-determined parameters such as a predetermined incubation time (for example 1 s to about 1 hour, for example about 1 min, 10 min, 15 min, 20 min or 30 min) and/or a pre-determined incubation temperature (for example 30-40° C., for example about 35° C., 36° C. or about 37° C.).

Red blood cells (erythrocytes) express a large number of antigens, some of which may be exploited in methods for detecting red blood cells. However, the red blood cell antigen profile varies depending on genetic background and red blood cells derived from one population or geographic locale may express an antigen profile which is different from that of red blood cells from other populations or different parts of the world. Red blood cells with different antigen profiles may be referred to as "red blood cell types". In humans, there are a number of different red blood cell types worldwide.

There are a number of 'high-frequency antigens' known to be present on the vast majority of red blood cells. However, while these antigens are present on most red blood cells, they are not present on all (or 100% of) red blood cells. Therefore, while it may be possible to detect a significant percentage of red blood cell types with a single agent capable of binding a single high frequency red blood cell antigen, methods of this type would fail to detect red blood cells which lack the antigen to which binding agent is specific. Even if the binding agent is specific to an antigen expressed by 99.9% of red blood cell types, the method would fail with 1 in 1,000 samples.

Thus, methods which are based solely on the use of binding agents which exhibit an affinity (or ability to bind) high frequency antigens may not achieve the detection of all, or substantially all, red blood cell types.

The present invention is based on the identification of antigens which are present on the majority of red blood cell types. Detection methods based on these antigens achieve detection of a greater percentage of red blood cell types as compared to prior art methods and/or methods based upon other antigens.

The antigen(s) which form the basis of the methods described in this invention are those that are expressed by about 99% to about 99.9% of all red blood cell types. For example, the antigen(s) exploited in the methods of this invention may be expressed by about 99.1%, about 99.2%, about 99.3%, about 99.4%, about 99.5%, about 99.6%, about 99.7% or about 99.8%.

For the avoidance of doubt, the methods provided by this invention may exploit any one of antigens (i)-(viii) and/or any agent capable of binding the same. Moreover, the invention may relate to methods which exploit combinations (for example 2 or more, perhaps for example 3, 4, 5, 6, 7 or all 8) of the antigens and/or agents capable of binding the same.

The term "sample" may be any sample containing red blood cells. For example, a sample may be a sample of whole blood or a sample of adult, foetal, neonatal and/or antenatal plasma, serum or red blood cells prepared therefrom. A "sample" may be any volume or amount of a fluid or substance which comprises, potentially comprises or is suspected of comprising, red blood cells. The samples may be biological and/or non-biological in nature or origin. For example, a "sample" may comprise any biological substance or fluid and the term may include samples of saliva, sweat, semen, faeces, tissue secretions, scrapings, biopsies and the like. Non-biological samples may include, for example, samples of soil, water and the like. A "sample", may be a forensic sample.

In addition, the present invention predominantly relates to the identification of human red blood cells; however, one of skill will appreciate that other (animal) sources of red blood cell may benefit from the invention provided the red blood cells express one or more of antigens (i)-(viii).

This invention may provide a control test for an assay. For example, this invention provides technology which may be used as a control to confirm the addition or application of red blood cells to an assay or other system. The invention may also be exploited in negative control tests so as to confirm the absence of red blood cells in a sample.

Many assays, including immunological assays require the addition of a sample of red blood cells. For example cross matching assays or blood typing assays may all require the addition of red blood cells. In assays of this type, it is advisable to include a test to demonstrate that the expected (or required) addition of red blood cells has been performed. This is especially important for microarray type assays where volumes are small and the addition of specific components and/or reagents cannot easily be determined by simple visual confirmation. Any test which serves to confirm the addition of a sample, reagent and/or component of an assay may be referred to as a "positive control". In the case of assays which require the addition of red blood cells, a positive control might be used to confirm the addition of the red blood cells. Should the result of the positive control test not confirm the addition of red blood cells, the assay would require to be repeated and/or the overall result should be invalidated.

As such, the invention provides a control test for an assay, said test comprising one or more binding agents capable of binding one or more of the red blood cell antigens selected from the group consisting of:
(i) En$^a$;
(ii) Ge:2;
(iii) Ge:3;
(iv) GPA;
(v) GPB;
(vi) H;
(vii) Rh29; and
(viii) Wr$^b$.

A control test of the type described above (and based on binding agents capable of binding one or more of the red blood cell antigens (i)-(viii)) may be used as a positive control test to confirm the addition of red blood cells to a process, a device, an apparatus, an assay and/or an assay system.

The various tests, methods, assays and products of this invention may exploit a specific selection of one or more of the binding agents described herein. For example, the invention may relate to tests, methods, assays and products exploiting or comprising, consisting or consisting essentially of, one or more binding agents capable of binding one or more of the red blood cell antigens selected from the group consisting of:
(i) H;
(ii) GPA; and
(iii) Rh29.

For example, the various aspects and embodiments of this invention may exploit anti-H binding agents, anti-Glycophorin A, B binding agents and/or anti-Rh29 binding agents. As stated elsewhere, the binding agents may be (polyclonal and/or monoclonal) antibodies or antigen binding fragments thereof.

Irrespective of the source or red blood cell type, the control test of this invention can more reliably report to the user the addition of red blood cells to a process, a device, an apparatus, an assay and/or an assay system. Without wishing to be bound by theory, the advantages of this invention may stem from the fact that the antigens which form the basis of this invention are expressed by the majority of red blood cell types. The improved reliability of the control test of this invention may be assessed relative to a prior art control test and/or a control test which is based upon binding agents which exhibit specificity for antigens different to those exploited in this invention. Thus, the control test of this invention may represent an improvement over other binding agent based control tests.

The binding agents for use in this invention exhibit specificity for red blood cell antigens. Binding agents which are specific to red blood cell antigens exhibit an ability to bind to one or more red blood cell antigen(s). Typically, a single binding agent is capable of binding a single red blood cell antigen. The methods of this invention may therefore use one or more binding agents in order to achieve the reliable detection (or capture) of red blood cells, wherein each binding agent is specific to one of the red blood cell antigens (i) to (viii).

A binding agent for use in this invention may be an antibody or an antigen binding fragment thereof, which exhibits specificity, affinity and/or an ability to bind, a red blood cell antigen (that antigen may be a factor common to the vast majority of red blood cells). Additionally, or alternatively, the binding agents may comprise other specifically reactive binding agents, such as for example, aptamers, small molecule antibody mimetics, nucleic acid ligands, or receptors from other cells which are capable of binding the red blood cell antigens, may be used. For example, lectins may also be used. For simplicity reference hereinafter will be made to binding agents and "antibodies", but this should not be construed as limiting.

The binding agents may comprise polyclonal and/or monoclonal antibodies. Polyclonal antibodies are heterogeneous populations of antibody molecules derived from the sera of animals/humans immunised with an antigen, or an antigenic/functional derivative thereof. For the production of polyclonal antibodies, host animals for example rabbits, sheep, pigs, etc., can be immunised by injection with a specific antigen. The injection further comprise (or be supplemented with) adjuvants.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein (1975), Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Antibodies and Cancer Therapy, Alan R. Liss, Inc., pp. 77-96).

Monoclonal antibodies for use in this invention can be of any immunoglobulin class including IgG, IgM, IgE, IgA, IgD and any subclass thereof. The hybridoma cell producing the mAb of this invention can be cultivated in vitro or in vivo. Production of high concentrations of mAbs in vivo makes this the presently preferred method of production.

Chimeric, single chain and humanised antibodies may also be used as binding agents in this invention. Techniques for the production of chimeric antibodies (Morrison et al., 1984, Proc. Natl. Acad. Sci., 81:6851-6855; Neuberger et al., 1984, Nature, 312:604-608; Takeda et al., 1985, Nature, 314:452-454; U.S. Pat. No. 4,816,567) comprise splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Techniques described for the production of single chain antibodies can be found in U.S. Pat. No. 4,946,778: Bird, 1988, Science 242:423-426; Huston et al., 1988, Proc. Natl. Acad. Sci. U.S.A. 85:5879-5883; and Ward et al., 1989, Nature 334:544-546. Techniques for making humanized monoclonal antibodies are described in U.S. Pat. No. 5,225,539 (incorporated in its entirety herein by reference).

Antibody fragments for use in this invention (which fragments exhibit an ability to bind an epitope) can be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries can be constructed (Huse et al., 1989, Science, 246:1275-1281) to allow rapid and easy identification of monoclonal Fab fragments with the desired specificity.

The invention may further exploit aptamers (small molecules, for example oligonucleotide/peptide molecules) with an ability to bind one or more of the red blood cell antigens described in this invention—in particular, antigens (i)-(viii).

All forms of antibody suitable for use in this invention, including those described above and antigen binding fragments thereof, shall be collectively referred to as "antibodies".

The binding agents for use in the invention may be immobilised, bound or adsorbed on to any suitable substrate. The binding agent may be immobilised, bound or adsorbed to all or part of a substrate. For example, the binding agent may be immobilised, bound or adsorbed to one or more discrete, predetermined locations on a substrate. For example, the binding agents may be immobilised as a plurality/series of distinct and/or discrete spots. For example, the binding agents may be immobilised, bound and/or adsorbed to a substrate as an array, for example a microarray. One of skill will appreciate that an array or microarray may comprise a plurality of discrete spots of immobilised, bound and/or adsorbed binding agent.

Each "spot" of immobilised binding agent may comprise the same or different binding agents. For example any given spot may comprise a single type of binding agent—for example a binding agent which is capable of binding a single red blood antigen. Alternatively, any given spot may comprise two or more binding agents, each binding agent being capable of binding a specific red blood cell antigen.

The methods of this invention may exploit a selection of immobilised binding agents, for example a selection of immobilised antibodies, which binding agents and/or antibodies exhibit specificity and/or an ability to bind one or more of antigens (i)-(viii).

The binding agents may be immobilised, bound or adsorbed (please note, the term "immobilised" may encompass "bound" and/or "adsorbed" binding agents) to any conventional substrate. The binding agents or antibodies for use may be immobilised to the substrate of an existing assay system—for example a crossmatching or blood typing assay system.

Substrates to which the binding agents or antibodies may be immobilised include, for example, those that are rigid or semi-rigid in nature. For example suitable substrates may include, membranes, filter, chips, slides, wafers, fibers, magnetic or nonmagnetic beads, gels, tubing, plates, polymers, microparticles and/or capillaries. The substrate can have a variety of surface forms, such as wells, trenches, pins, channels and pores, to which the binding agents and/or antibodies are immobilised/bound. As described in more detail below the substrate surface architecture may be formed and adapted to improve or facilitate fluorescent based detection methods. Substrates of this type are described in WO02/059583 and WO03/023377. Accordingly, substrates for use may be optically transparent.

The binding agents and/or antibodies for use in this invention may be immobilised on or to substrates which comprise, for example, glass, silicon, silicon oxide, metals and metal oxides either bare or (at least partially) functionalised with functional polymers such as, for example, glycidoxypropyltriethoxysilane, poly-1-lysine, aminopropylsilane, carboyxsilane, hydrogels and polymer-brushes, self-assembled monolayers of e.g. functionalised alkyl thiols. A substrate for use may comprise silane based coating for example, a silane compound with a hydrophobil linkage and functional group with the ability to bind to biological molecules of interest.

As described above, the binding agents and/or antibodies for use in this invention may be bound or immobilised to a substrate in an array. As used herein the term "array" refers to a generally ordered arrangement of immobilised, bound or adsorbed probes (for example binding agents and/or antibodies), on a substrate such as glass.

Typically the array may be in the form of a series of regularly spaced apart delimited, distinct and/or discrete areas to which the binding agents or antibodies are bound. Substrate bound antibody arrays may be commonly described as "antibody chips".

The antibodies may be arranged on, for example, a flat or spherical substrate referred hereto as a "chip". The methods of this invention may exploit a single type of binding agent or antibody or a plurality of different antibodies. Thus at least one but perhaps at least 2, 3 or 4 different antibodies may be bound to the surface of the substrate. Moreover, each specific antibody may be provided in a number of dilutions and/or repeated a number of times (e.g. 3-10 times).

Substrates used to prepare "antibody chips" for use in this invention may comprise small planar substrates. Suitable planar substrates may be any suitable size. For example a planar substrate for use in this invention may be anywhere between about 5 mm and about 100 mm in length and about 5 mm to about 50 mm in width. For example, a suitable planar substrate may be about 76 mm by about 26 mm or about 12.5 mm by about 7.9 mm in size.

The binding agent or antibody may be applied to a substrate by spotting or printing. Suitable known techniques, include those described by Michael J. Heller, Annual Review of Biomedical Engineering, 2002 Vol. 4: 129-153. DNA Microarray Technology: Devices, Systems and Applications and Angenendt, P.; Glökler, J.; Murpy, D.; Lehrach, H.; Cahill, D. J. Anal. Biochem., 2002, 309, 252-260 Angendt, P.; Glökler, J.; Sobek, J.; Lehrach, H.; Cahill, D. J. Chromatogr. A, 2003 100, 997-104.

Spotted or printed spots of binding agent/antibody may be less than 1 mm in diameter, such as less that 500 μm or 100 μm in diameter or between about 50 μm and about 1000 μm in diameter. In this manner 10 s to 1000 s of individual and discrete binding agent/antibody spots may be provided on the surface of any given substrate.

For the avoidance of doubt any one location or spotted/printed spot on a substrate of this invention may comprise a single binding agent/antibody type or two or more binding agent/antibody types.

Each binding agent of the various methods, tests, assays and/or products described herein may be provided at a single or multiple different concentrations. For example, in the case of a microarray test or assay, each location or spotted/printed spot may comprise one or more binding agents at or in one or more amounts or concentrations. For example, any given spot or location on a microarray may contain a binding agent at or in a particular concentration. Another spot or location on the same array may contain the same binding agent at or in the same amount or different concentration. Any given spot may contain two or more binding agents each provide at or in the same amount or concentration or at or in different amounts or concentrations.

As stated, binding agents for use in this invention may be printed onto substrates. The various binding agents may be printed at the required concentration. For example a binding agent specific for the H antigen (an anti-H antibody for example) may be printed at about 1-20 µg/mL (or at about any specific amount therebetween), about 5-15 µg/mL or at about 6, 7, 8, 9, 10, 11, 12, 13 or 14 µg/mL.

A binding agent specific for Glycophorin A, B (an anti-GPA/GPB antibody for example) may be printed at a concentration of about 1-50 µg/mL (or at about any specific amount therebetween), about 10-40 µg/mL, about 20-40 µg/mL or at about 25-35 µg/mL A binding agent specific for Rh29 (an anti-Rh29 antibody for example) may be printed at a concentration of about 1-100 µg/mL (or at about any specific amount therebetween), about 10-90 µg/mL, about 20-80 µg/mL, about 30-60 µg/mL. For example, an anti-Rh29 binding agent (antibody) may be printed at a concentration of about 50, 51, 52, 53, 54 or 55 µg/mL.

Furthermore, it should be understood that other assay systems, including other arrays and/or microarrays may be supplemented with one or more of the binding agents (which are each specific for one or more of the red blood cell antigens (i)-(viii)) described above. For example an assay or assay system including arrays and microarrays, may comprise a control test which itself comprises one or more of the binding agents of this invention.

Various procedures are well known in the art for immobilising binding agents and/or antibodies of the type described herein, to the surface of a substrate. For example, electrostatic binding may be used to immobilise antibodies. Other methods which may be used to immobilise or attach a binding agent or antibody to a surface include hydrophobic/hydrophillic interactions, chemical interactions, and amine coupling. Binding agents and antibodies may be adsorbed directly onto gold containing substrates via sulphur containing amino acids (cysteine, methionine), or through binding via alkanethiols which comprise functional groups to interact with the binding agents, previously bound to the gold containing substrate.

Areas of the substrate surface which are not provided with binding agent and which could provide non-specific binding sites are desirably treated with blocking agents in order to prevent any non-specific binding of components other than red blood cells present in a sample. For example, antibodies, proteins, peptides, complement factors and the like may all non-specifically bind to unblocked areas of a substrate. Suitable blocking agents are well known in the art and may comprise albumin or serum (free of undesirable antibodies such as blood group antibodies, anti-IgG antibodies or those that could interfere with any test probe interactions), non-fat milk protein, casein, bovine serum albumin (BSA) and the like. The blocking agents may be formulated or prepared for use with a suitable buffer.

For example, a suitable blocking agent may comprise, 1% w/v bovine serum albumin (BSA) (PPA, Austria) in Phosphate Buffered Saline (PBS) (0.15 M sodium chloride, 2.632 M Phosphate Buffer Stock Solution (Quotient, Scotland), pH 7.0).

Optionally coated substrates prepared for use may be stored as dried substrates. Additionally or alternatively, the substrates may be stored at ambient temperature or under refrigerated/freezing conditions.

The methods of this invention may be conducted in a microarray format. Moreover, one or more of the binding agents provided by this invention may be incorporated into a microarray system as part of, for example, a control test. The ability to provide the methods of this invention in microarray format is advantageous as microarray type assays represent efficient and effective alternatives to conventional large format assays. The microarray methods/assays of this invention may easily be integrated into other tests (for example other microarray tests) important in blood processing—including, for example, blood group phenotyping tests for multiple antigens on the surface of the red blood cell.

One of skill will appreciate that microarray assays which require the addition of red blood cells may not exploit standard control tests to confirm the addition of red blood cells. The volumes/amounts of samples and other components added to a microarray assay are small and it is difficult and/or impossible to use visual means to confirm the addition of red blood cells. By exploiting binding agents such as antibodies, the methods described herein, represent an effective, rapid and sensitive means of detecting red blood cells and/or confirming the addition of red blood cells in microarray type assays.

The presence of red blood cells bound to the (immobilised) binding agents or antibodies of this invention may be detected by means of various techniques known in the art such as, for example, secondary labelling detection which may exploit fluorescent, chemiluminescent conjugated antibodies.

Fluorescence may be detected by any suitable photodetector known in the art, such as a spectrophotometer or digital imaging device such as, for example a CCD image sensor (in the form of a CCD camera) or a CMOS sensor. Conveniently there may be used a simple flatbed scanner with the red blood cell (erythrocyte) binding being detected by the scanner and the intensity thereof given a visual output for interpretation or a numerical value for purposes of interpretation and data processing.

Conveniently bound red blood cells may be detected by means of the autofluorescence of the RBCs as described in C J Campbell et al., 2006. Detection by autofluorescence has the particular advantage of avoiding the need for the use of any labelling and providing a particularly simple form processing. In more detail the RBCs may be irradiated or excited with light of wavelength about 420 nm, 488 nm, 543 nm or 580 nm, and fluorescent emission detected at a longer wavelength such as 530 nm if excited at 488 nm or 570-585 nm if excited at 543 nm.

Thus, in this invention, bound red blood cells (erythrocytes) may be detected by a fluorescent signal or by image generation following scanning using, for example, a flatbed scanner.

It will be appreciated that by knowing the position/location of each of the binding agents/antibodies of this invention on a substrate, it is possible to (a) determine whether or not red blood cells are present in a sample or (b) confirm the addition of red blood cells to an assay or assay system.

One of skill in this field will understand that using appropriate electronics and software, any device can be programmed to know the identity and location of a specific spot, binding agent(s) and/or antibody on or immobilised to the surface of a substrate and to correlate this with signals generated, so that a particular binding can be determined and identified to the tester. Additionally, statistical software may be included so as to combine and formulate the results from the various repetitions and/or dilutions of the binding agents/antibodies provided on the substrate. In this manner, the signals obtained from a multiplicity of specific antibody spots may be factored together and a statistically significant result displayed to the tester.

In a further aspect, the invention provides an assay or a device for the detection of red blood cells, said assay or device, comprising a substrate having immobilised thereon one or more binding agents capable of binding one or more red blood cell antigens selected from the group consisting of:

(i) $En^a$;
(ii) Ge:2;
(iii) Ge:3;
(iv) GPA;
(v) GPB;
(vi) H;
(vii) Rh29; and
(viii) $Wr^b$.

The invention may provide a method of crossmatching blood samples, said method comprising a control test as described herein. As stated, a control test suitable for use in a crossmatching assay may comprise one or more of the binding agents described herein, which binding agents are specific to one or more of red blood cell antigens (i)-(viii).

A method of crossmatching blood samples, may comprise:

providing plasma or serum from a first blood sample;
contacting the plasma sample with red blood cells from a second blood sample to provide a plasma/red blood cell mix;
incubating the plasma/red blood cell mix under conditions which permit sensitisation of the red blood cells;
separating the red cells from a liquid phase; and
contacting the red cells with an agent capable of binding antibodies;
wherein the separation of the red cells from a liquid phase takes place without centrifugation and the detection of sensitised red blood cells bound to the agent capable of binding antibodies indicates that the donor blood is incompatible with the blood of the intended recipient.

In a method of this type, a control test of the type described herein may be used to determine, confirm or monitor the addition of red blood cells to each stage of the method. For example, a control test of this invention may be used to confirm (i) the addition of red blood cells to a plasma sample and/or (ii) the addition of red blood cells to the agent capable of binding antibodies. For example, as a sample of the separated red blood cells is added to the agent capable of binding antibodies, a further sample of the separated red blood cells may (simultaneously or concurrently) be added to one or more binding agents capable of binding one or more of antigens (i)-(viii).

The crossmatching assay may exploit a substrate upon which spots of agent capable of binding antibodies (for example spots of anti-human immunoglobulin antibody) have been immobilised—perhaps, in the form of a microarray. The substrate may further comprise one or more (additional) spots comprising binding agents or antibodies with specificity to one or more of the antigens provided by this invention. These additional "spots" may form the basis of a control test which can be used to confirm the addition of red blood cells (some of which may have become sensitised through prior incubation steps) to the substrate.

As such, the invention provides a substrate for use in a blood crossmatching assay, the substrate having immobilised thereon one or more binding agents capable of binding antibodies and one or more binding agents capable of binding one or more of red blood cell antigens (i)-(viii). The substrate may be any substrate described herein and the various binging agents may be immobilised thereto by or using any of the standard technologies available (including those described above). The binding agents may be immobilised in discrete, pre-determined regions locations or spots as an array or microarray. Each location or spot may comprise a single type of binding agent (for example a binding agent with specificity to a single antigen or antibody) or multiple different types of binding agent (with collective specificity for one or more antigens or antibodies). Furthermore, each spot may solely comprise binding agents capable of binding antibodies (for use in cross matching) or binding agents capable of binding red blood cell antigens (for example antigens (i)-(viii): for use as control tests).

An exemplary crossmatching assay which can be supplemented with a control test of this invention is identified in patent applications GB1402174.5 filed Jul. 2, 2014 and PCT/GB2015/050338 filed 6 Feb. 2015. For convenience, the entire contents of these applications is reproduced below in the section headed "Crossmatching Method".

DETAILED DESCRIPTION

Figure 1:
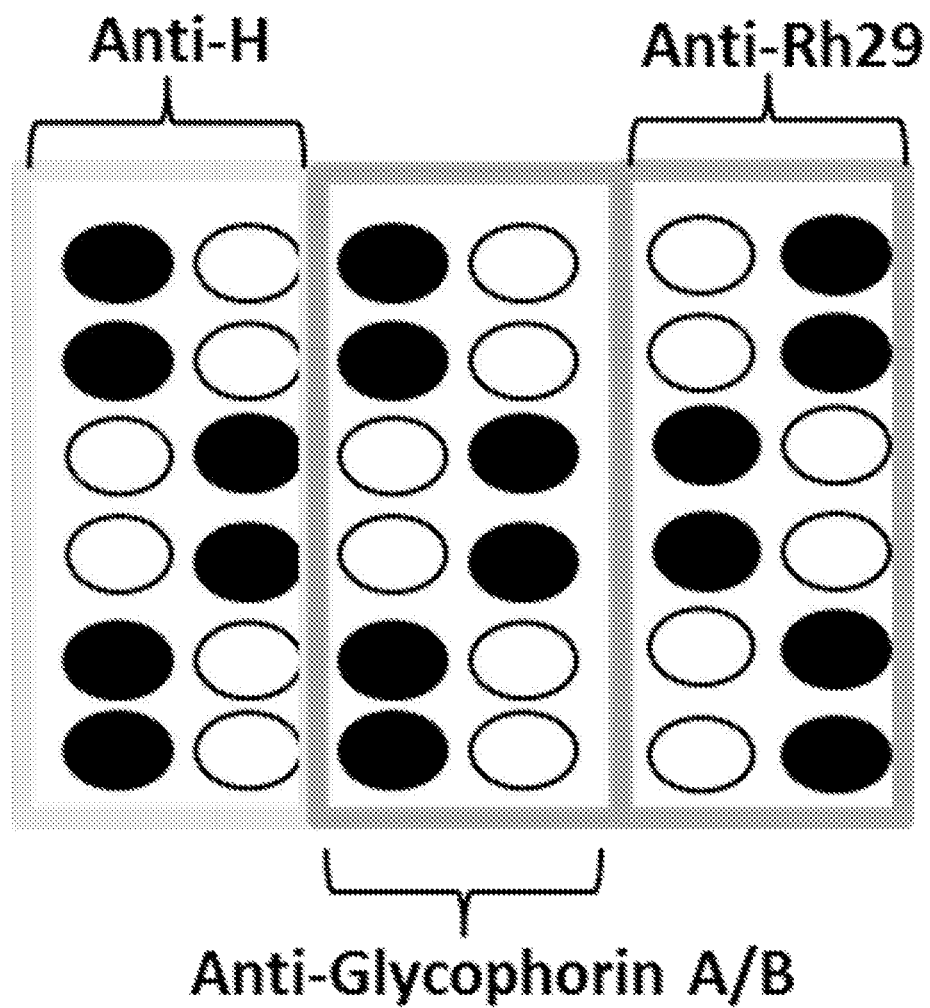
FIG. 1: Diagrammatic representation of a single array (6 x 6 grid of spots) showing the three antibodies printed. Anti-H was printed at 11 μg/mL, anti-Glycophorin A,B at 35 μg/mL and anti-Rh29 at 54 μg/mL. 16 arrays were printed on each side in a 2 x 8 format. Black spots indicate a positive cell binding response and white spots indicate 50% glycero/PBS printed as negative spots which should not bind any cells.

The present invention will now be described in detail with reference to the following Figures which show:

FIG. 1: Diagrammatic representation of a single array (6×6 grid of spots) showing the three antibodies printed. Anti-H was printed at 11 μg/mL, anti-Glycophorin A,B at 35 μg/mL and anti-Rh29 at 54 μg/mL. 16 arrays were printed on each slide in a 2×8 format. Black spots indicate a positive cell binding response and white spots indicate 50% glycerol/PBS printed as negative spots which should not bind any cells.

Figure 2:
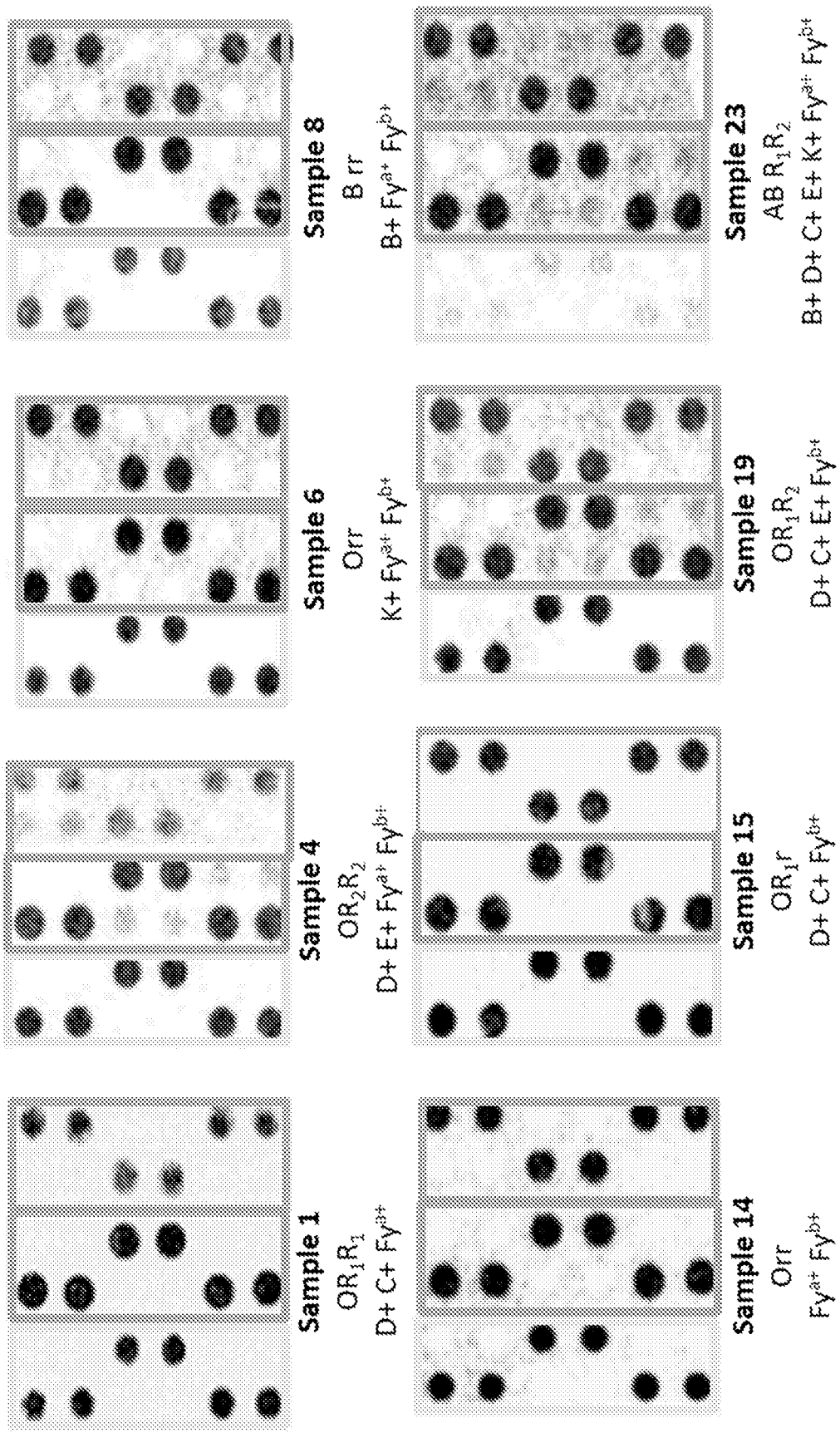
FIG. 2: Microarray images of responses from anti-H, anti-Glycophorin A,B and anti-Rh29 for 16 samples which represent a proportion of the total 56 samples tested.
Figure 2:
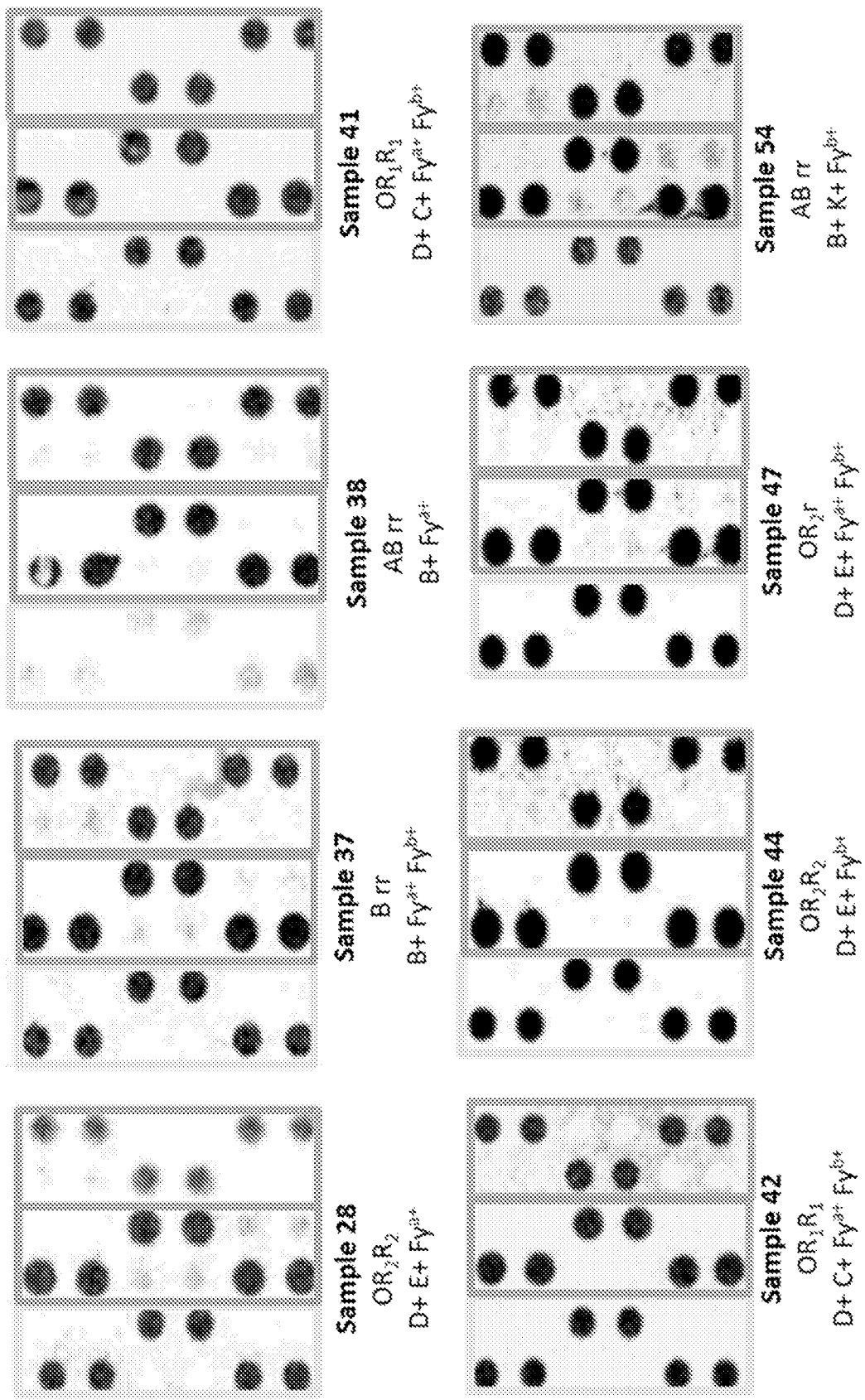

FIG. 2: Microarray images of responses from anti-H, anti-Glycophorin A,B and anti-Rh29 for 16 samples which represent a proportion of the total 56 samples tested.

High Frequency Antigens—for Use in Red Blood Cell Addition Controls Probability Calculations Highlighted (bold/underlined) antigens represent exemplary targets for binding agents/antibodies, for use in methods (including control tests) described herein. Nevertheless, it should be understood that any of the antigens identified below represent possible targets for useful binding agents/antibodies.

Summary of Scenarios for Calculations:
- Ideally binding agents/antibodies will be selected from different blood group systems
- Seven antibody specificities have been identified, but from six blood group systems
- Assuming a 100% confidence in the antibody performance
- Assumptions for the calculation: each antibody, coming from six blood groups, is assumed to be distributed independently across the whole of the human population. In practice, this could be untrue if, for example, the antibodies are at linkage disequilibrium (the genes encoding them are chromosomally close).

If the independence assumption is accepted, the formula for calculating the frequency of a completely negative sample, i.e. one where the individual under study doesn't have any of the listed antigens, is simply the product of the individual's chance for not carrying each of them independently. Thus: if the individual doesn't have antigen 1 and antigen 2 as in Scenario 1, the frequency of such genetic makeup in the general population is $(1-99.9\%)*(1-99.9\%)=0.001*0.001=1$ in a million. Similarly, for scenario 2 it is $(1-99.9\%)*(1-99.9\%)*(1-99.9\%)=1$ in a billion, and so on and so forth. The following table summarises the numbers (the numbers are approximately correct for 5 and/or 6 antibodies in the panel).

| Combination of antibodies | Number of antibody in blend | | | | | | Frequency of negative sample: | Frequency of negative sample (abbrev.) |
|---|---|---|---|---|---|---|---|---|
| | 1 | 2 | 3 | 4 | 5 | 6 | | |
| Scenario 1 | 99.9% | 99.9% | — | — | — | — | 1 in 1,000,000 | 1 in 1e+06 |
| Scenario 2 | 99.9% | 99.9% | 99.9% | — | — | — | 1 in 1,000,000,000 | 1 in 1e+09 |
| Scenario 3 | 99.9% | 99.9% | 99.9% | 99.9% | — | — | 1 in 1,000,000,000,000 | 1 in 1e+12 |
| Scenario 4 | 99.9% | 99.9% | 99.9% | 99.9% | 99.9% | — | 1 in 999,999,999,999,996 | 1 in 999999999999996 |
| Scenario 5 | 99.9% | 99.9% | 99.9% | 99.9% | 99.9% | 99.9% | 1 in 999,999,999,999,994,752 | 1 in 999999999999994752 |
| Scenario 6 | 99.0% | 99.9% | — | — | — | — | 1 in 100,000 | 1 in 1e+05 |
| Scenario 7 | 99.0% | 99.9% | 99.9% | — | — | — | 1 in 100,000,000 | 1 in 1e+08 |
| Scenario 8 | 99.0% | 99.9% | 99.9% | 99.9% | — | — | 1 in 100,000,000,000 | 1 in 1e+11 |
| Scenario 9 | 99.0% | 99.9% | 99.9% | 99.9% | 99.9% | — | 1 in 100,000,000,000,000 | 1 in 1e+14 |
| Scenario 10 | 99.0% | 99.9% | 99.9% | 99.9% | 99.9% | 99.9% | 1 in 99,999,999,999,999,472 | 1 in 99999999999999472 |

| Antigen | 'Worldwide' frequency % | Specific frequency characteristics | Frequency of target/antigen Frequency % (positive) to be used for calculations | Number of antigen-negativedonors per 100. | Reference for frequency | Comments on antibody availability |
|---|---|---|---|---|---|---|
| AnWj | 100 | 3 negatives found, 2 in Israeli woman and 1 Arab-Israeli family. | 99.9 | <1 | 901 series of high incidence antigens. Blood group antigen factsbook (2012). Reid, M. E., Lomas-Francis, C. and Olsson, M. Third Edition. Academic Press. Page 684. Blood group antigens & antibodies (2007). Reid, M. E. and Lomas-Francis, C. SBB Books. Page 12. | unknown |
| At$^a$ | 100 | >99% blacks | 99.0 | <1 | 901 series of high incidence antigens. Blood group antigen factsbook (2012). Reid, M. E., Lomas-Francis, C. and Olsson, M. Third Edition. Academic Press. Page 682. | Unknown |
| Cr$^a$ | 100 | 99% Native Americans. | 99.0 | All populations: none Blacks < 1 | 'Other useful facts'. Blood group antigen factsbook (2012). Reid, M. E., Lomas-Francis, C. and Olsson, M. Third Edition. Academic Press. Page 699. Blood group antigens & antibodies (2007). Reid, M. E. and Lomas-Francis, C. SBB Books. Page 28. | Unknown |
| Di$^b$ | 100 | 100% all populations. 96% American Indians. 99% Hispanics. | 99.9 | <1 | Diego. Blood group antigen factsbook (2012). Reid, M. E., Lomas-Francis, C. and Olsson, M. Third Edition. Academic Press. Page 390. Blood group antigens & antibodies (2007). Reid, M. E. and Lomas-Francis, C. SBB Books. Page 36. | Unless anti-Band 3 available. No good source of Anti-Di$^b$ at the moment. |
| DISK | 100 | Only one negative reported in Irish. | 99.9 | <1 | Diego. Blood group antigen factsbook (2012). Reid, M. E., Lomas-Francis, C. and Olsson, M. Third Edition. Academic Press. Page 414. | Unknown |
| Dr$^a$ | 100 | Negatives only found in Jews from Bukhara, and Japanese. | 100 | 0 | Cromer. Blood group antigen factsbook (2012). Reid, M. E., Lomas-Francis, C. and Olsson, M. Third Edition. Academic Press. Page 534. Blood group antigens & antibodies (2007). Reid, M. E. and Lomas-Francis, C. SBB Books. Page 39. | Unknown |
| Emm | N/A | Only 6 examples of negatives found/known. | 99.9 | <1 | 901 series of high incidence antigens. Blood group antigen factsbook (2012). Reid, M. E., Lomas-Francis, C. and Olsson, M. Third Edition. Academic Press. Page 683. | unknown |

| | | | | | | |
|---|---|---|---|---|---|---|
| En$^a$ (lacks GPA) | 100 | RBCs lacking GPA/Ena have reduced levels of sialic acid. | 99.9 | 0 | MNS. Blood group antigen factsbook (2012). Reid, M. E., Lomas-Francis, C. and Olsson, M. Third Edition. Academic Press. Page 109. Blood group antigens & antibodies (2007). Reid, M. E. and Lomas-Francis, C. SBB Books. Page 42. | Monoclonal available. |
| Es$^a$ | 100 | Random <99%. Es(a−) probands 3 known. Mexican/South American/Black 99% | 99.0 | <1 | Cromer. Blood group antigen factsbook (2012). Reid, M. E., Lomas-Francis, C. and Olsson, M. Third Edition. Academic Press. Page 535. Blood group antigens & antibodies (2007). Reid, M. E. and Lomas-Francis, C. SBB Books. Page 43. | Unknown |
| Ge:2 | >99.9 | Antigen lacking from all Gerbich negative individuals. | 99.9 | <1 | 'Other useful facts'. Blood group antigen factsbook (2012). Reid, M. E., Lomas-Francis, C. and Olsson, M. Third Edition. Academic Press. Page 699. Blood group antigens & antibodies (2007). Reid, M. E. and Lomas-Francis, C. SBB Books. Page 49. | Anti-Ge:2 available |
| Ge:3 | >99.9 | N/A | 99.9 | <1 | 'Other useful facts'. Blood group antigen factsbook (2012). Reid, M. E., Lomas-Francis, C. and Olsson, M. Third Edition. Academic Press. Page 699. Blood group antigens & antibodies (2007). Reid, M. E. and Lomas-Francis, C. SBB Books. Page 50. | Anti-Ge:3 available |
| GPA | See En$^a$ | See En$^a$ | See En$^a$ | See En$^a$ | MNS. Blood group antigen factsbook (2012). Reid, M. E., Lomas-Francis, C. and Olsson, M. Third Edition. Academic Press. Page 109. | Anti-GPA monoclonal available |
| GPB | 99 | Same as U neg. 99.9 in Caucasians, 99% in blacks | 99 | <1 | MNS. Blood group antigen factsbook (2012). Reid, M. E., Lomas-Francis, C. and Olsson, M. Third Edition. Academic Press. Page 72. | Anti-GPB monoclonal available |
| GUTI | 100 | Only two negatives reported. | 99.9 | 0 | Cromer. Blood group antigen factsbook (2012). Reid, M. E., Lomas-Francis, C. and Olsson, M. Third Edition. Academic Press. Page 542. | Unknown |
| Gy$^a$ | 100 | N/A | N/A | 0 | Blood group antigens & antibodies (2007). Reid, M. E. and Lomas-Francis, C. SBB Books. Page 52. | Unknown |
| H | 99.9 | H-deficient: 1/8000 Taiwanese, 1/150,000 Japanese, 1/10,000 India, 1/1,000,000 Europeans. | 99.9 | <1 | Hh. Blood group antigen factsbook (2012). Reid, M. E., Lomas-Francis, C. and Olsson, M. Third Edition. Academic Press. Page 497. Blood group antigens & antibodies (2007). Reid, M. E. and Lomas-Francis, C. SBB Books. Page 53. | Monoclonals antibodies available |
| hr$^B$ | 98 | All populations: R$_2$R$_2$ lack hr$^B$ Blacks: 97% | 97.0 | 2 | Blood group antigens & antibodies (2007). Reid, M. E. and Lomas-Francis, C. SBB Books. Page 57. | unknown |
| Hr$^B$ | 99 | N/A | 99.0 | <1 | Blood group antigens & antibodies (2007). Reid, M. E. and Lomas-Francis, C. SBB Books. Page 58. | unknown |
| hr$^S$ | 98 | All populations: 98% as R$_2$R$_2$ lack hr$^S$ Blacks: 97% | 98.0 | 2 | Blood group antigens & antibodies (2007). Reid, M. E. and Lomas-Francis, C. SBB Books. Page 59. | Unknown |
| Hy | 100 | >99% blacks | 99.0 | 0 | Dombrock. Blood group antigen factsbook (2012). Reid, M. E., Lomas-Francis, C. and Olsson, M. Third Edition. Academic Press. Page 449. Blood group antigens & antibodies (2007). Reid, M. E. and Lomas-Francis, C. SBB Books. Page 60. | Unknown |
| I | >99 adults | N/A | 99.0 | <1 | I. Blood group antigen factsbook (2012). Reid, M. E., Lomas-Francis, C. and Olsson, M. Third Edition. Academic Press. Page 607. Blood group antigens & antibodies (2007). Reid, M. E. and Lomas-Francis, C. SBB Books. Page 61. | I-like monoclonal available. |
| IFC (Cr$_{null}$) | >99 | N/A | 99.0 | <1 | Cromer. Blood group antigen factsbook (2012). Reid, M. E., Lomas-Francis, C. and Olsson, M. Third Edition. Academic Press. Page xxx. Blood group antigens & antibodies (2007). Reid, M. E. and Lomas-Francis, C. SBB Books. Page 63. | Unknown |

-continued

| | | | | | | |
|---|---|---|---|---|---|---|
| In$^b$ | 100% | 96% in Indians (South Asia) | N/A | 0 | Indian. Blood group antigen factsbook (2012). Reid, M. E., Lomas-Francis, C. and Olsson, M. Third Edition. Academic Press. Page 572.<br>Blood group antigens & antibodies (2007). Reid, M. E. and Lomas-Francis, C. SBB Books. Page 66. | Unknown |
| Jo$^a$ | 100 | >99% blacks | 99.0 | 0 | Dombrock. Blood group antigen factsbook (2012). Reid, M. E., Lomas-Francis, C. and Olsson, M. Third Edition. Academic Press. Page 450.<br>Blood group antigens & antibodies (2007). Reid, M. E. and Lomas-Francis, C. SBB Books. Page 72. | unknown |
| MAM | N/A | Only 4 negatives reported. | N/A | N/A | 901 series of high incidence antigens. Blood group antigen factsbook (2012). Reid, M. E., Lomas-Francis, C. and Olsson, M. Third Edition. Academic Press. Page 689. | unknown |
| PEL | N/A | PEL negative found in only two families | N/A | N/A | 901 series of high incidence antigens. Blood group antigen factsbook (2012). Reid, M. E., Lomas-Francis, C. and Olsson, M. Third Edition. Academic Press. Page 688. | unknown |
| Rh29 | 100 | Rh$_{null}$ phenotypes are negative for Rh29. | 99.9 | 0 | Rh. Blood group antigen factsbook (2012). Reid, M. E., Lomas-Francis, C. and Olsson, M. Third Edition. Academic Press. Page 228. | Monoclonal antibody available. |
| Wr$^b$ | 100% | N/A | 99.9 | <1 | Diego. Blood group antigen factsbook (2012). Reid, M. E., Lomas-Francis, C. and Olsson, M. Third Edition. Academic Press. Page 392.<br>Blood group antigens & antibodies (2007). Reid, M. E. and Lomas-Francis, C. SBB Books. Page 144. | Monoclonal antibodiesavailable. |

Preparation of Protein Microarrays

Coated slides obtained from Schott were used as the substrate. The antibody probe samples to be spotted were prepared in 50% Glycerol/50% PBS. The slides were printed using an Arrayjet Sprint Arrayer (Arrayjet) with a 12 sample Jetspyder. Replicates of each antibody were printed on each slide separated by negative control spots of 50% glycerol/PBS—see FIG. 1. All slides were printed within a relative humidity between 40-60%, and at an ambient temperature (20-23° C.). Printed probes were left to immobilise in the humidified atmosphere for 30 minutes prior to being stored in a box at 2-8° C. in the dark for at least 24 hours.

Preparation of Red Cells for Use in the Microarray Assay

All 56 EDTA samples were tested by a serological tube technique for a wide range of specificities prior to being frozen as per a validated in-house protocol. Required samples were defrosted and retested by tube technique to verify the specificity of the samples. The recovery of cells was sufficient to prepare the required volume of red cell suspension for each sample.

All cell types were suspended in PBS or washed into LISS (low ionic strength saline)—other diluents may be used, including, for example Modified Alsevers, and variations thereof. Moreover, cells need not be washed—rather a small volume of cells may be removed from the donor sample (which has perhaps been centrifuged) directly into PBS buffer. Where washing was used, cells were centrifuged three times at 3000 rpm for 2 minutes using a Thermo Centra CL2 centrifuge with the supernatant removed each time and replaced with approximately 4 mL PBS. After the final centrifugation, one wash in PBS was performed before re-suspending the cells to 2% HCT in PBS. The cells were further diluted to 1% HCT in diluent.

Antigen Typing (AT) Assay Protocol

Printed array slides were removed from 2-8° C. storage and fitted into Grace-Bio 16-well manifolds ensuring both central and straight alignment of the arrays in each well, secured using the metal clips and fitted into a Proplate tray (3 slide type). Slides were returned to storage at 2-8° C. until immediately prior to use. Blocking solution (2% BSA/PBS) was warmed to approx. 37° C. Slides were blocked by adding 160 μL of blocking solution to each well and incubated at 37° C. with shaking at 350 rpm on a Grant Bio PHMP Thermoshaker for 15 minutes (with plastic cover).

After blocking, the solution was removed and 160 μL of 1% HCT cells in diluent (from Examples 2) were slowly pipetted into the left hand side of each appropriate well. Slides were incubated stationary at 37° C. for 15 minutes (with plastic cover). Following incubation, the whole Proplate tray containing slides was dipped into a tub of PBS. Suction may be used to remove the PBS and any other fluid in the wells.

Slides were carefully removed from the Grace-Bio manifold and transferred to a slide holder and submerged into fresh PBS. Optionally slides may be fixed by immersion in 0.1% gluteraldehyde/PBS for 10 minutes at 2-8° C., or more conveniently the PBS is removed by suction and analysis performed directly using the flatbed scanner. This was followed by a final wash in water before centrifuged to dryness. Slides stored in a dust-free dark place until scanning.

Anti-H was shown to be responsive to all samples tested. FIG. 2 shows that all samples showed a positive response, however the response observed for AB type blood samples (sample 23 and 38) were weaker. The antigen profile of these cells is probable group $A_1B$, where less H is present due to the efficient conversion of H antigen to $A_1$ or B antigen occurring.

The responses for anti-Glycophorin A,B were positive for all samples tested.

The response for anti-Rh29 observed for cells that had the Rh type $OR_2R_2$ (samples 4 and 28) show weaker responses than all other cell types tested. Printing of these antibodies in a blend or as a combination of two or more may find application in control tests where all antibodies were blended at optimum concentration. Because of the rarity of negative control samples for these three separate antigen profiles, none were tested using this technique.

REFERENCES

Robb. J. S., Roy, D. J., Ghazal, P., Allan, J. and Petrik, J. (2006). "Development of non-agglutination microarray blood grouping" Transfusion Medicine. 16, 119-129.

Campbell, C. J., O'Looney, N., Chong Kwan, M., Robb, J. S., Ross, A. J., Beattie, J. S., Petrik, J. and Ghazal, P. (2006). "Cell Interaction Microarray for Blood Phenotyping" Analytical Chemistry. 78, 1930-1938.

UK Blood Transfusion Services. (2013). Guidelines for the Blood Transfusion Services in the United Kingdom. 8$^{th}$ Edition. The Stationary Office, Norwich.

British Committee for Standards in Haematology; Milkins, C., et al. (2013). Guidelines for pre-transfusion compatibility procedures in blood transfusion laboratories. Transfusion Medicine 23, 3-35.

Cross Matching Method

The present disclosure provides novel methods for the detection of antibodies—in particular, blood group antibodies. The methods may be applied to pre-transfusion blood compatibility testing for the detection of incompatibility between donor units (comprising donor red blood cells (erythrocytes)) and a recipient.

Red blood cells can appear "foreign" to a host immune system if they express antigens not found on the red blood cells of that host. It is for this reason that blood must be carefully crossmatched before it is transfused. For example, some red blood cells express A type antigens; blood in which the red blood cells express the A blood group antigen is referred to as blood group "A". Other blood groups include "B" (where the erythrocytes express the "B" blood group antigen), "AB" (where the erythrocytes express both the A and B blood group antigens) and O (where the erythrocytes do not express either the A or B blood group antigens). As explained in more detail below, an incompatibility between donor red blood cells (erythrocytes) and a recipient depends upon the presence of antibody in the recipient plasma which bind to antigens present on red blood cells. Incompatibility testing may be referred to as "crossmatching".

A complete crossmatch depends not only on the presence or absence of anti-A or anti-B antibodies in plasma, but also on other antibodies with affinity for other antigens expressed by red blood cells/erythrocytes (including, but not limited to, Rh, Kell and the like).

If incompatible donor blood is transfused, the recipient's immune system (specifically those circulating antibodies with affinity for the antigens present on the "foreign", transfused, blood) will "attack" the incompatible blood and the transfusion may fail. Moreover, the mass destruction of the donor blood can induce inappropriate and/or exaggerated immune responses and the clotting system cascades. Shock, kidney failure and even death may occur following an incompatible transfusion.

When a sample of recipient plasma is incubated with an incompatible source of red blood cells, antibodies in the plasma with specificity for the "foreign" red blood cell antigens, bind to those antigens and "coat" the red blood cells. This process is known as sensitisation and red blood cells with antibody bound to surface antigen are referred to as "sensitised erythrocytes" or "sensitised red blood cells".

Red blood cells (erythrocytes) sensitised with antibody (protein) can withstand the processing steps required to execute an immunological assay. Indeed, sensitised red blood cells (erythrocytes) subjected to immunological assays and other processing procedures may remain 'sensitised' (coated) with antibody throughout the various incubation and washing steps. In view of the above, the process of sensitisation can be exploited as the basis of an immunological crossmatching test.

In a first aspect, the disclosure provides a method of crossmatching blood samples, said method comprising:
providing plasma or serum from a first blood sample;
contacting the plasma sample with red blood cells from a second blood sample to provide a plasma/red blood cell mix;
incubating the plasma/red blood cell mix under conditions which permit sensitisation of the red blood cells;
separating the red cells (some or all of which of which, may or may not be sensitised) from a liquid phase; and
contacting the sensitised red cells with an agent capable of binding antibodies;
wherein the separation of the sensitised red cells from a liquid phase takes place without centrifugation and the detection of sensitised red blood cells bound to the agent capable of binding antibodies indicates that the donor blood is incompatible with the blood of the intended recipient.

As explained above, the crossmatching methods disclosed herein may further comprise a control test comprising binding agents that bind one or more of antigens (i)-(viii)

It should be understood that the sensitisation of the red blood cells occurs through binding between (for example, anti-blood group antigen) antibodies present in the plasma and antigens (for example blood group antigens) of the red blood cells.

Plasma or serum for use may be prepared from whole blood using any suitable or standard preparation protocol. Where the method is a method for crossmatching blood, the plasma and/or serum may be provided by, or derived from, a patient who is to receive a blood transfusion. In order to prepare plasma for use, whole blood may be collected into anticoagulant-treated tubes. Red blood cells and platelets are removed or separated by centrifugation and the resulting supernatant is designated plasma. A plasma sample for use may comprise, for example, a volume of about 10 μL to about 1 mL. For example, about 100 μL, 150 μL, 160 μL, 200 μL, 250 μL or 300 μL of plasma may be used. To prepare serum for use, whole blood may be collected and allowed to clot for a period of time. Again, red blood cells and platelets are removed by centrifugation and the resulting supernatant is designated serum. Plasma and/or serum for use in the methods disclosed herein may be diluted with a suitable buffer or diluent prior to use. Plasma and/or serum may be prepared for use as a 1:1, 1:2, 1:3, 1:4, 1:5, 1:6, 1:7, 1:8, 1:9 or 1:10 dilution. Suitable diluents may include, for example, phosphate buffered saline (PBS) and/or low ionic strength solution (LISS).

Red blood cells for use may be derived from any suitable source of whole blood. Where the method is a method for crossmatching blood for transfusion, the red cells may be obtained from a source of donor blood which is intended for use. Donor blood may be collected and stored in flexible plastic bags. The bags may contain compounds and chemicals (for example sodium citrate, phosphate, dextrose, and sometimes adenine) which prevent the blood from clotting and facilitate storage. The tubing through which blood passes into the storage bag may be segmented after collection to provide "pigtail" sections which contain small volumes of blood. These small "pigtail" volumes of donor blood are suitable for use in crossmatching assays, including the assays disclosed herein. Small volumes of whole blood may be provided as a source of red blood cells for use in the assays. For example, about 1 ul to about 500 ul or red blood cells may be used. The crossmatching assays may use about 10 μL, 20 μL, 30 μL, 40 μL, 50 μL, 60 μL, 70 μL, 80 μL, 90 μL or 100 μL of whole blood. Prior to use, the red blood cells may be diluted with any suitable diluent or buffer.

The plasma and/or serum and red blood cells may be mixed to provide a plasma/red blood cell mixture. For convenience, the plasma/serum and red blood cell mix will be referred to as a "cell mix". The cell mix may be further diluted using a suitable buffer or medium. For example, the cell mix may be diluted using low ionic strength solution (LISS). Suitable dilutions of the cell mix may include, for example 1:1, 1:2, 1:3, 1:4; 1:5 or 1:6 dilutions with buffer (LISS for example).

The (optionally diluted) cell mix, may be incubated under conditions which permit antibodies present in the plasma or serum (for example anti-blood group antigen antibodies) to interact with and bind to antigens present on the surface of the red blood cells. As mentioned above, red blood cells to which antibodies, for example, anti-blood group antigen antibodies have bound, are referred to as "sensitised" red blood cells. Thus, the incubation of the cell mix may be conducted under conditions suitable to permit or allow the formation of sensitised red blood cells. Further, the conditions may include a predetermined time and/or a predetermined temperature. For example, the cell mix may be incubated at about 30-40° C., for example 37° C. and/or for about 10 seconds to several hours. The cell mix may be incubated at about 37° C. for about 5 min, about 10 min, about 15 min, about 20 min, about 25 min or about 30 min.

The cell mix may be prepared and/or incubated in or on any suitable substrate, vessel, tube, plate (including multi-well plates) and/or slide. The cell mix may be prepared and/or incubated on or in glass and/or plastic substrates, vessels, tubes, plates and/or slides. Substrates, vessels, plates and/or slides (whether glass, plastic or comprising some other material) may be coated and/or blocked to prevent or reduce non-specific binding between plasma/serum and/or whole blood components and the material of the substrate, vessel, tube, plate or slide.

For reasons outlined above, crossmatching assays must be both sensitive and specific. In particular it is important that instances of false positive and/or negative results are brought to within certain tolerance levels or occur at no greater frequency that what would be regarded as acceptable. One of skill will appreciate that in the case of a crossmatching assay, false negative results would suggest that donor blood is compatible when, in fact, the donor blood may be incompatible. In a method of this disclosure, a false negative result may occur if the process used to detect sensitised red blood cells becomes blocked, neutralised or otherwise inhibited. The process used to detect sensitised red blood cells requires a binding agent (for example an antibody) that has affinity for antibodies. Binding agents of this type may be blocked, neutralised and/or prevented from interacting with sensitised red blood cells by antibody present in plasma and/or serum.

As such, the presence of unbound plasma/serum antibodies with specificity for red blood cell (erythrocyte) antigens present in the cell mix must be (substantially) removed from the remainder of the methods disclosed herein.

Typically, the occurrence of false negative results in immunological (including crossmatching) assays is prevented by frequent washing and/or centrifugation steps. This ensures that after any initial period of incubation between a plasma/serum sample and a source of red blood cells (to produce sensitised red blood cells), any unbound antibodies present in the plasma/serum are not carried through to the final stages of the assay where they can neutralise the binding agents (for example antibodies) used to detect the sensitised red blood cells. Washing steps facilitate the removal of unbound antibody from an assay whereas centrifugation affects the separation of unbound antibodies in liquid phase from those which have bound their target.

While washing and/or centrifugation steps represent effective means to reduce instances of false negative and/or positive results in immunological assays, including assays of the type described herein, they are time consuming and increase the amount of peripheral equipment required to complete the assay.

The present disclosure represents an improvement as it provides a sensitive, specific, accurate and rapid assay for crossmatching blood, which assay achieves a rate or level of false positive and/or false negative results comparable with prior art crossmatching assays and tests but with reduced use of washing and/or centrifugation steps.

This is, in part, achieved by conducting the cell mix incubation step under conditions which permit the separation of the red cell component of the cell mix from the liquid phase of the cell mix. For example, the incubation may be conducted under conditions which facilitate the settling of the cells (some, all or none of which may be sensitised) to form, for example, a pellet. The settling of the cells and/or formation of a pellet may leave a liquid phase or supernatant comprising antibodies which have not bound to red blood cell antigens and other plasma or serum components. The formation of a pellet of red blood cells permits easy separation of the red blood cells (or a sample thereof) from the liquid phase (or supernatant) such that the remainder of the assay can be conducted on the red blood cell component and in the absence of plasma or serum components which, as described above, may lead to false negative and/or false positive results.

The methods of this disclosure and in particular the cell mix incubation step, avoids the use of centrifugation to form the cell pellet or to separate the red cells (some, all or none of which may be sensitised) from the liquid phase of the cell mix and any unbound antibody. Rather, the red blood cells are allowed to separate from the liquid phase and settle over time and/or under gravity. This may result in the formation of a natural red blood cell pellet or clump. Once a pellet of red blood cells has formed and settled, the user may perform either or both of the following actions. The supernatant may be removed leaving only the red blood cells, some of which may have become sensitised by anti-blood group antigen antibodies during the cell mix incubation step. Additionally or alternatively, a settled or pelleted red blood cells or a sample thereof, may be removed. The remainder of the assay is then performed on those red blood cells remaining after removal of the supernatant or the red blood cells removed from the red cell mix.

The inventors have surprisingly found that once the red blood cells have pelleted and/or settled, removal of the liquid phase/supernatant by, for example pipetting or decanting or removal of the settled/pelleted red blood cells (or a sample thereof) by, for example, suction is sufficient (an no additional washing is required before the cells are resuspended in buffer for application to the binding agents) to ensure that the methods of this disclosure exhibit a similar, comparable (or perhaps even better) occurrence or level of false positive and/or negative results as observed in (or with) prior art assays. Thus, without wishing to be bound by theory, it is suggested that removal of the supernatant or liquid phase or removal of the settled/pelleted red blood cells (or a sample thereof) is sufficient to remove unbound plasma/serum antibody from the assay to such an extent that the binding agents used in the detection of sensitised red blood cells, do not become neutralised.

The red blood cells for use in the remainder of the method of this disclosure may be re-suspended in a suitable buffer before being brought into contact with agents capable of binding antibodies. A suitable red blood cell re-suspension buffer may comprise, for example bovine serum albumin and/or LISS.

The optionally re-suspended red blood cells (some of which may have become sensitised) are contacted with agents capable of binding antibodies. For example, if the method is conducted using human samples (human plasma and human donor blood) the binding agents capable of binding antibodies should be capable of binding human antibodies. Binding agents for use may be antibodies or antigen binding fragments thereof, with specificity for one or more antibody isotypes. For example, a single antibody type specific to a single antibody isotype (immunoglobulin G, M, A, E or D for example) or a plurality of different antibodies each with specificity for a different antibody isotype.

The agent capable of binding sensitised red blood cells may itself be an antibody or an antigen binding fragment thereof, which exhibits specificity and/or affinity for one or more other antibodies coating (sensitising) a red blood cell. Additionally, or alternatively, other specifically reactive binding agents, such as for example, small molecule antibody mimetics, nucleic acid ligands, or receptors from other cells which are capable of binding sensitised red blood cells, may be used. Lectins may also be employed. For simplicity reference hereinafter will be made to binding agents and "antibodies", but this should not be construed as limiting.

It will be appreciated that the choice of binding agent (for example antibody) used in will depend on the nature of the antibodies coating (sensitising) the red blood cells. For example, the binding agent may be any agent capable of binding a plasma/serum antibody or any other component present in plasma or serum which might sensitise (bind to) a red blood cell. For example, the binding agents may comprise agents capable of binding immunoglobulin and/or complement factors. In general the binding agents used would correspond to those used in conventional DAT or IAGT testing i.e. at least anti-$IgG_1$, anti-$IgG_3$, and anti-Complement (C3) or a broad spectrum anti-human IgG, of either monoclonal or polyclonal source. Advantageously, anti-$IgG_2$ and $IgG_4$ antibodies may be used. If desired other antibodies could also be included such as for example, anti-light chain λ, or anti-light chain κ antibodies.

The methods may use polyclonal and/or monoclonal antibodies. Polyclonal antibodies are heterogeneous populations of antibody molecules derived from the sera of animals immunised with an antigen, or an antigenic functional derivative thereof. For the production of polyclonal antibodies, host animals for example rabbits, sheep, pigs, etc., can be immunised by injection with a specific antigen optionally supplemented with adjuvants.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein (1975), Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Antibodies and Cancer Therapy, Alan R. Liss, Inc., pp. 77-96).

Monoclonal antibodies for use can be of any immunoglobulin class including IgG, IgM, IgE, IgA, IgD and any subclass thereof. The hybridoma producing the mAb can be cultivated in vitro or in vivo. Production of high titers of mAbs in vivo makes this the presently preferred method of production.

Chimeric, single chain and humanised antibodies may also be used as binding agents. Techniques for the production of chimeric antibodies (Morrison et al., 1984, Proc. Natl. Acad. Sci., 81:6851-6855; Neuberger et al., 1984, Nature, 312:604-608; Takeda et al., 1985, Nature, 314:452-454; U.S. Pat. No. 4,816,567) comprise splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Techniques described for the production of single chain antibodies can be found in U.S. Pat. No. 4,946,778: Bird, 1988, Science 242:423-426; Huston et al., 1988, Proc. Natl. Acad. Sci. U.S.A. 85:5879-5883; and Ward et al., 1989, Nature 334:544-546. Techniques for making humanized monoclonal antibodies are described in U.S. Pat. No. 5,225,539 (incorporated in its entirety herein by reference).

Antibody fragments for use (which fragments recognise specific epitopes) can be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries can be constructed (Huse et al., 1989, Science, 246:1275-1281) to allow rapid and easy identification of monoclonal Fab fragments with the desired specificity.

The methods may exploit a monoclonal anti-IgG, monoclonal anti-$IgG_1$, a monoclonal anti-$IgG_3$, and a monoclonal anti-C3. When anti-IgG is included, this is conveniently a (polyclonal or monoclonal) anti-IgG. A blend of these probes may also be used to give the same result, without differentiation of type of antibody bound.

All forms of antibody suitable for use, including those described above, shall be collectively referred to as "antibodies".

The binding agents, including any antibodies used, may be bound or immobilised to or on a substrate. Any conventional substrate may be used in the crossmatching methods. Suitable substrates include those that are rigid or semi-rigid in nature. For example suitable substrates may include, membranes, filter, chips, slides, wafers, fibers, magnetic or nonmagnetic beads, gels, tubing, plates, polymers, microparticles and/or capillaries. The substrate can have a variety of surface forms, such as wells, trenches, pins, channels and pores, to which the binding agents and/or antibodies are immobilised/bound. As described in more detail below and depending on methods used to affect the detection of bound sensitised red blood cells (erythrocytes), the substrate surface architecture may be formed and adapted to improve or facilitate fluorescent based detection methods. Substrates of this type are described in WO02/059583 and WO03/023377. Accordingly, substrates for use may be optically transparent.

Suitable substrates may include those comprising glass, silicon, silicon oxide, metals and metal oxides either bare or functionalised with functional polymers such as, for example, glycidoxypropyltriethoxysilane, poly-1-lysine, aminopropylsilane, carboyxsilane, hydrogels and polymer-brushes, self-assembled monolayers of e.g. functionalised alkyl thiols. A suitable substrate may comprise silane based coating for example, a silane compound with a hydrophobil linkage and functional group with the ability to bind to biological molecules of interest.

Binding agents and/or antibodies for use may be bound or immobilised to a substrate in an array. As used herein the term "array" refers to a generally ordered arrangement of bound probes (for example binding agents and/or antibodies), that specifically bind to sensitised red blood cells (or rather the antibodies which coat/sensitise the red blood cells), on a substrate such as glass.

Typically the array may be in the form of a series of regularly spaced apart delimited areas to which the binding agents or antibodies are bound. Such substrate bound antibody arrays may be commonly described as "antibody chips".

The antibodies may be arranged on, for example, a flat or spherical substrate referred hereto as a "chip". The methods may exploit a single type of binding agent or antibody or a plurality of different antibodies. Thus at least one but perhaps at least 2, 3 or 4 different antibodies may be bound to the surface of the substrate. Moreover, each specific antibody may be provided in a number of dilutions and/or repeated a number of times (e.g. 3-10 times), in order to further minimise any false positive or negative reactions which may occur, when carrying out a method of detection.

Substrates used to prepare "antibody chips" for use may comprise small planar substrates. Suitable planar substrates may be any suitable size. For example a planar substrate for use may be anywhere between about 5 mm and about 100 mm in length and about 5 mm to about 50 mm in width. For example, a suitable planar substrates may be about 76 mm by about 26 mm or about 12.5 mm by about 7.9 mm in size.

The binding agent or antibody may be applied to the substrate by spotting or printing. Suitable known techniques, include those described by Michael J. Heller, Annual Review of Biomedical Engineering, 2002 Vol. 4: 129-153. DNA Microarray Technology: Devices, Systems and Applications and Angenendt, P.; Glökler, J.; Murpy, D.; Lehrach, H.; Cahill, D. J. Anal. Biochem., 2002, 309, 252-260 Angendt, P.; Glökler, J.; Sobek, J.; Lehrach, H.; Cahill, D. J. Chromatogr. A, 2003 100, 997-104.

Spotted or printed spots of binding agent/antibody may be less than 1 mm in diameter, such as less that 500 μm or 100 μm in diameter or between about 50 μm and about 1000 μm in diameter. In this manner 10 s to 1000 s of individual and discrete binding agent/antibody spots may be provided on the surface of any given substrate.

For the avoidance of doubt any one location or spotted/printed spot on a substrate may comprise a single binding agent/antibody type or two or more binding agent/antibody types.

Various procedures are well known in the art for immobilising binding agents and/or antibodies of the type described herein, to the surface of a substrate. For example, electrostatic binding may be used to immobilise antibodies. Other methods which may be used to immobilise or attach a binding agent or antibody to a surface include hydrophobic/hydrophillic interactions, chemical interactions, and amine coupling. Binding agents and antibodies may be adsorbed directly onto gold containing substrates via sulphur containing amino acids (cysteine, methionine), or through binding via alkanethiols which comprise functional groups to interact with the binding agents, previously bound to the gold containing substrate.

Areas of the substrate surface which are not provided with binding agent and which could provide non-specific binding sites are desirably treated with blocking agents in order to prevent any non-specific binding of antibodies, complement factors (and other plasma derived components), red blood cells or sensitised RBCs. Suitable blocking agents are well known in the art and may comprise albumin or serum (free of undesirable antibodies such as blood group antibodies, anti-IgG antibodies or those that could interfere with any test probe interactions on the same microarray), non-fat milk protein, casein, bovine serum albumin (BSA) and the like. The blocking agents may be formulated or prepared for use with a suitable buffer.

For example, a suitable blocking agent may comprise, 1% w/v bovine serum albumin (BSA) (ID Bio, France) in Phosphate Buffered Saline (PBS) (0.15 M sodium chloride, 2.632 M Phosphate Buffer Stock Solution (Quotient, Scotland), pH 7.0).

Optionally coated substrates prepared for use may be stored for use as dried substrates. Additionally or alternatively, the substrates may be stored at ambient temperature or under refrigerated/freezing conditions.

In view of the above, the crossmatching methods may be conducted in a microarray format. Microarray crossmatching assays represent efficient and effective alternatives to conventional crossmatch testing. Moreover, microarray crossmatching assays may be readily integrated into other tests (for example other microarray tests) important in blood processing—including, for example, blood group phenotyping for multiple antigens on the surface of the red blood cell (erythrocyte).

Following incubation under conditions which permit binding between sensitised red blood cells and the immobilised binding agents and/or antibodies, unbound red blood cells may be removed by, for example, washing.

The presence of the captively held (bound) sensitised red blood cells (erythrocytes) may be detected by means of various techniques known in the art such as, for example, secondary labelling detection which may exploit fluorescent, chemiluminescent conjugated antibodies.

Fluorescence may be detected by any suitable photodetector known in the art, such as a spectrophotometer or digital imaging device such as, for example a CCD image sensor (in the form of a CCD camera) or a CMOS sensor. Conveniently there may be used a simple flatbed scanner with the red blood cell (erythrocyte) binding being detected by the scanner and the intensity thereof given a visual output for interpretation or a numerical value for purposes of interpretation and data processing.

Conveniently bound sensitised red blood cells may be detected by means of the autofluorescence of the RBCs as described in C J Campbell et al., 2006. Detection by autofluorescence has the particular advantage of avoiding the need for the use of any labelling and providing a particularly simple form processing. In more detail the RBCs may be irradiated or excited with light of wavelength about 420 nm, 488 nm, 543 nm or 580 nm, and fluorescent emission detected at a longer wavelength such as 530 nm if excited at 488 nm or 570-585 nm if excited at 543 nm.

Thus, in this disclosure, bound sensitised red blood cells (erythrocytes) may be detected by a fluorescent signal or by image generation following scanning using, for example, a flatbed scanner.

It will be appreciated that by knowing the position of each specific antibody on the substrate, it is possible to determine whether or not donor red blood cells erythrocytes have been sensitised by antibodies present in patient plasma samples. For the avoidance of doubt, compatible donor units yield negative results (no sensitisation thus no cells bound) whereas incompatible donor units yield positive results (sensitisation, therefore positive detection of bound sensitised red blood cells). One of skill in this field will understand that using appropriate electronics and software, any device can be programmed to know the identity and location of specific antibodies on the surface of the substrate and to correlate this with signals generated, so that a particular binding can be determined and identified to the tester. Additionally, statistical software may be included so as to combine and formulate the results from the various repetitions and/or dilutions of the antibodies provided on the substrate. In this manner, the signals obtained from a multiplicity of specific antibody spots may be factored together and a statistically significant result displayed to the tester.

The methods may include one or more controls. For example, a positive control may be used confirm the addition of red blood cells. A positive control may comprise anti-erythrocyte antibodies. The anti-erythrocyte antibodies may be immobilised and/or spotted/printed onto a substrate as described in more detail above.

It should be understood that the methods described herein, in particular the processing of a cell mix into (sensitised) red blood cell and liquid phases without the use of centrifugation and/or wash steps, may be exploited in a number of different immunological assays. For example, any assay which requires the incubation of a source of antibodies and red blood cells (erythrocytes) and the subsequent detection of sensitised red blood cells (erythrocytes: forming during incubation between the antibody source and the red blood cells), may benefit from the procedures described herein. Thus the disclosure may provide a means of providing red blood cells for use in a method of detecting sensitised red blood cells the method comprising incubating red blood cells and a composition capable of sensitising red blood cells (for example a composition comprising antibodies and/or complement components, for example plasma or serum) under conditions which facilitate the sensitisation of the red blood cells and the settling under gravity of the red blood cell component; and removing the liquid phase (or supernatant) and/or removing at least a sample of the red blood cells.

Further preferred features and advantages of the disclosure will appear from the following detailed Examples given by way of illustration.

DETAILED DESCRIPTION

Figure 3:
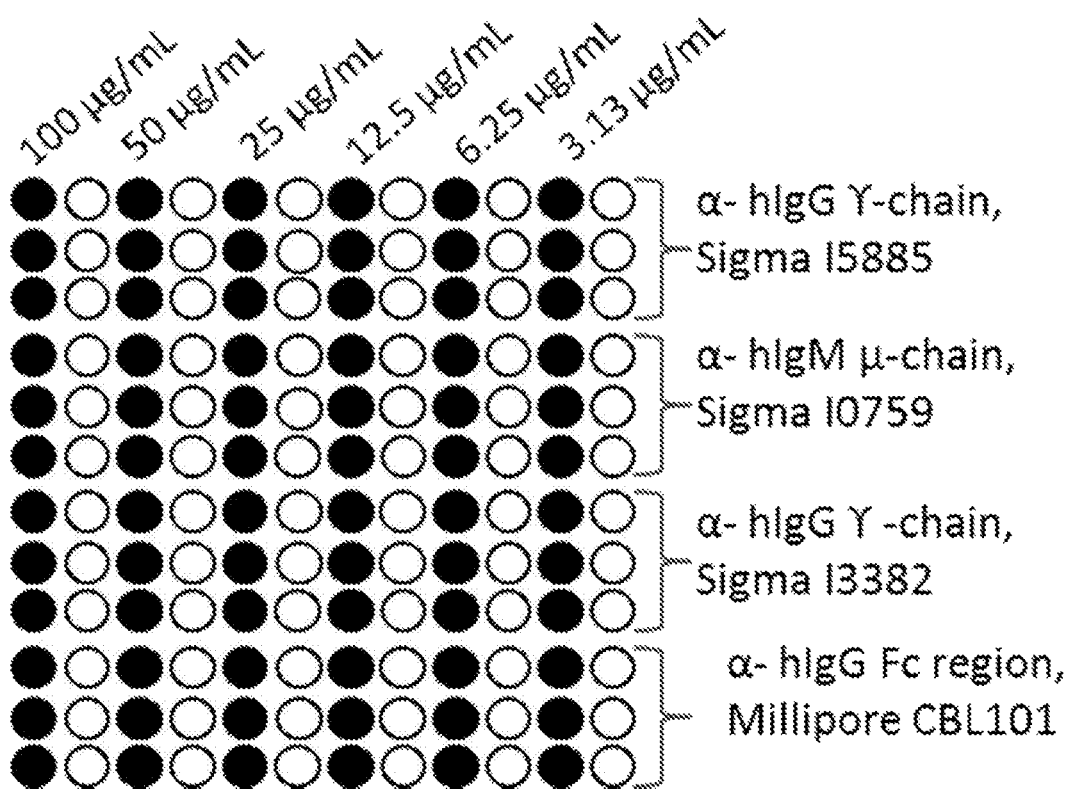

FIG. 3: Diagrammatic representation of a single array (12×12 grid of spots) showing the antibodies printed. 16 arrays were printed on each slide in a 2×8 format. Black spots indicate antibody printed (in triplicate) and white spots indicate 50% glycerol/PBS printed as negative spots.

Figure 4:
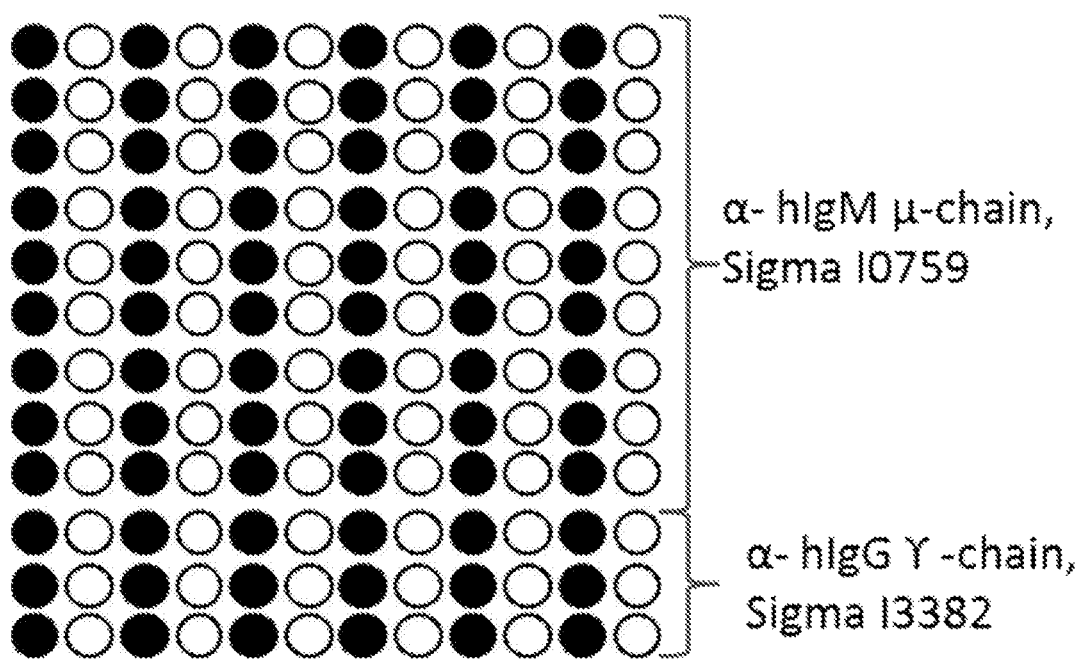

FIG. 4: Diagrammatic representation of a single array (12×12 grid of spots) showing the two antibodies printed. α-hIgM was printed at 518 μg/mL and α-hIgG at 301 μg/mL. 16 arrays were printed on each slide in a 2×8 format. Black spots indicate a positive cell binding response and white spots indicate 50% glycerol/PBS printed as negative spots which should not bind any cells.

Figure 5:
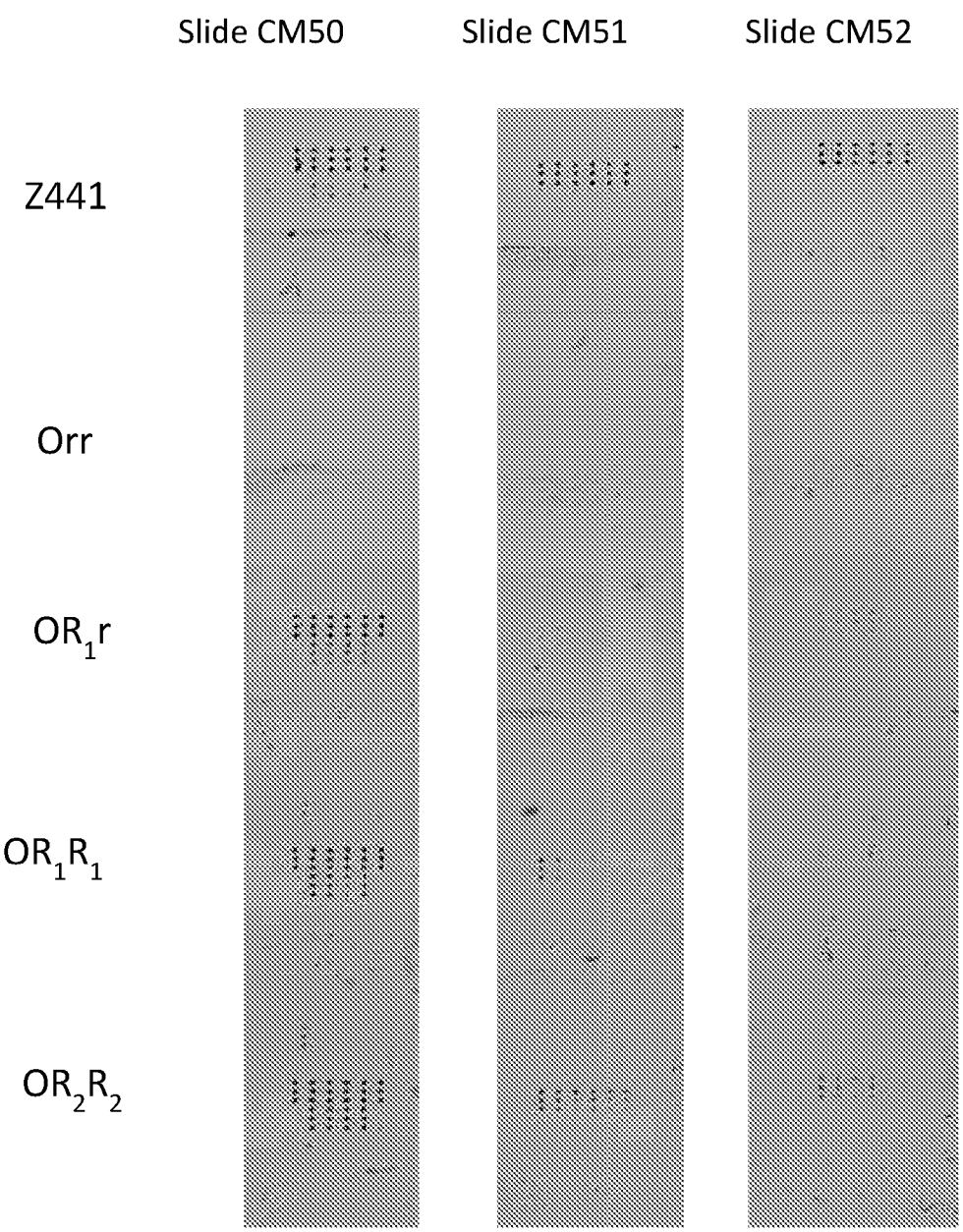

FIG. 5: Image of slides CM50, CM51 and CM52 showing the results for Orr, $OR_1r$, $OR_1R_1$ and $OR_2R_2$ cells sensitised with anti-D plasma for 30 minutes using the tube, glass slide or plate technique respectively. Also shown are the results for the positive control cells (Z441, IgG Sensitised Cells).

Figure 6:
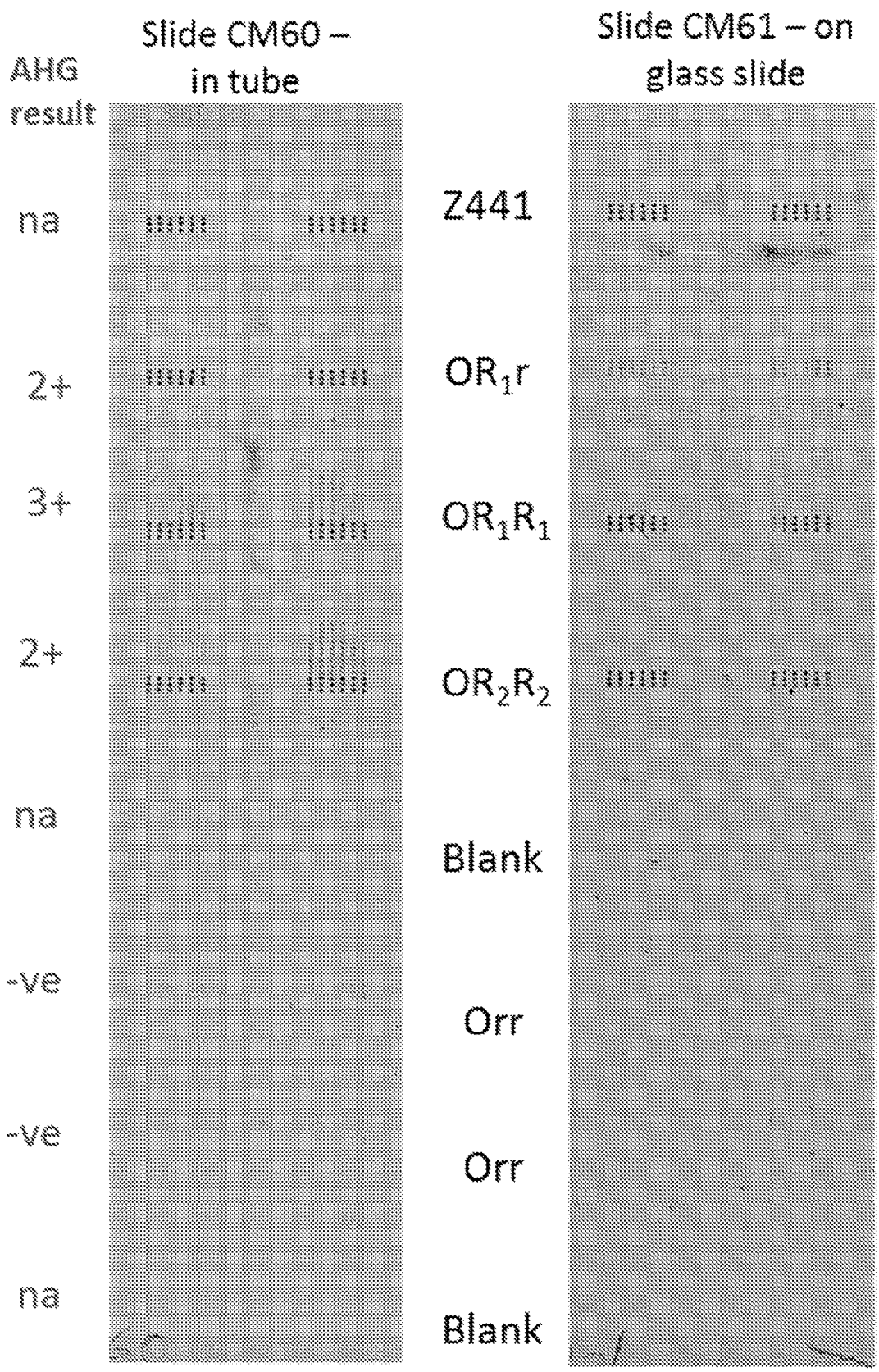

FIG. 6: Image of slides CM60 and CM61 showing the results for $OR_1r$, $OR_1R_1$, $OR_2R_2$ and Orr cells sensitised with anti-D plasma for 30 minutes using the tube or glass slide technique respectively. Also shown are the results for the positive control cells (Z441, IgG Sensitised Cells) and the agglutination grading results from the indirect agglutination testing using AHG (AHG result=reference technique).

Figure 7:
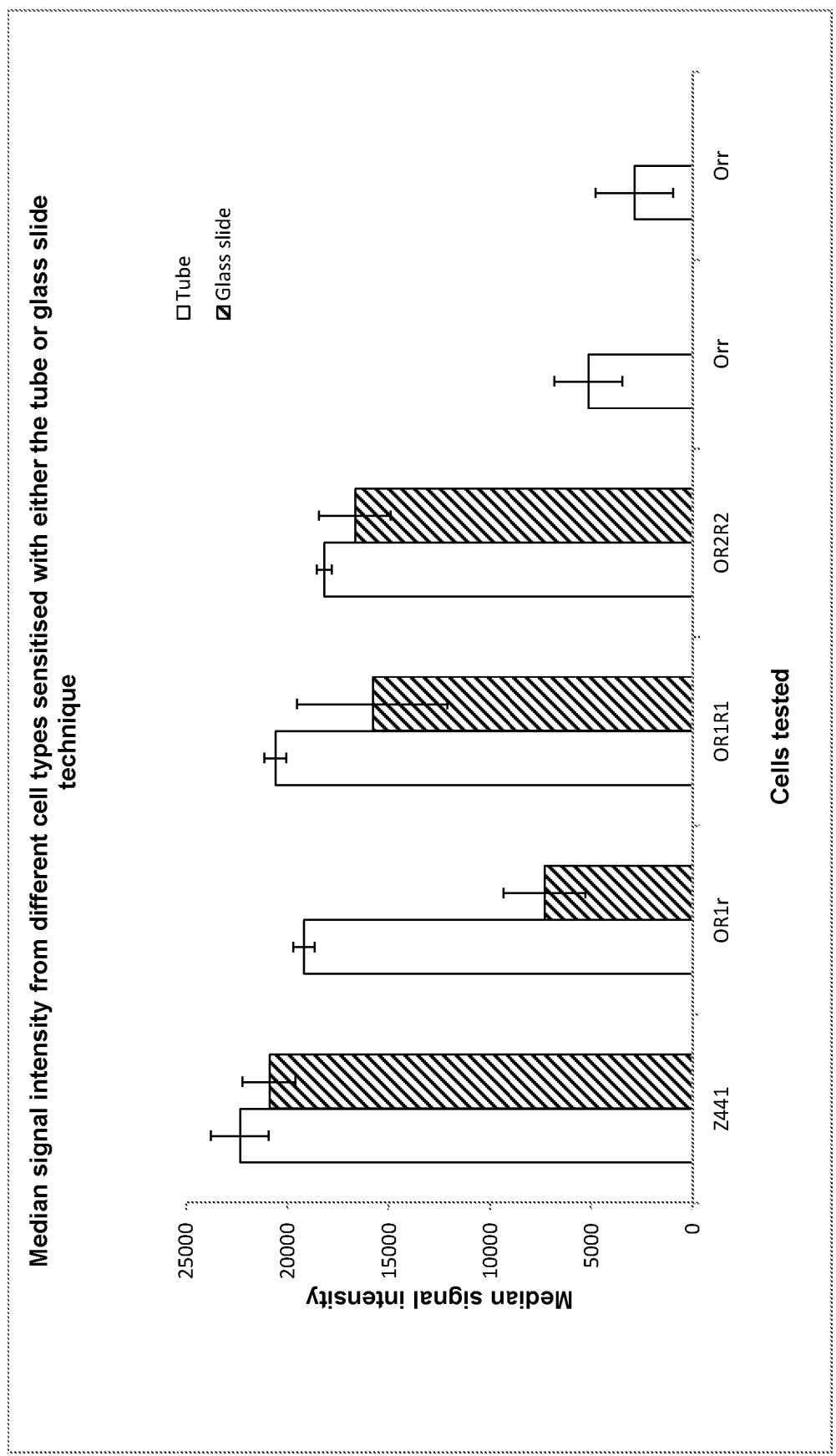

FIG. 7: Data generated from images shown in FIG. 6, showing the median signal intensity for the cells tested to the α-hIgG printed in the array. The results for the tube or glass slide technique are shown with the standard deviation of the median signal intensity plotted.

Figure 8A:
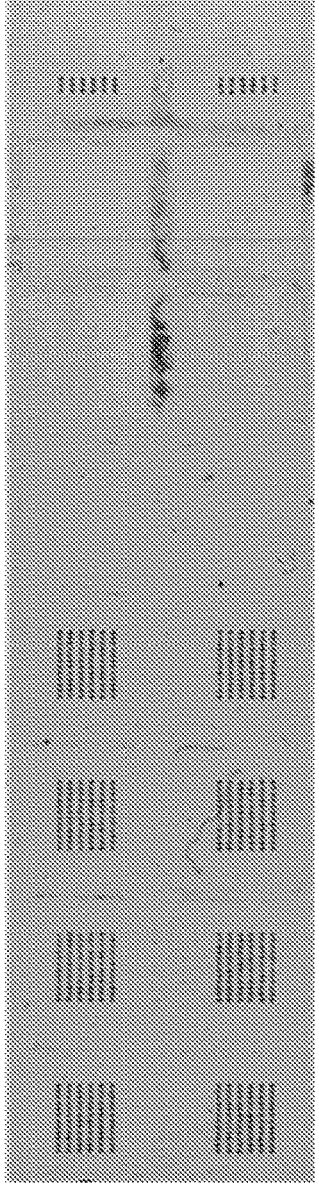
Figure 8B:
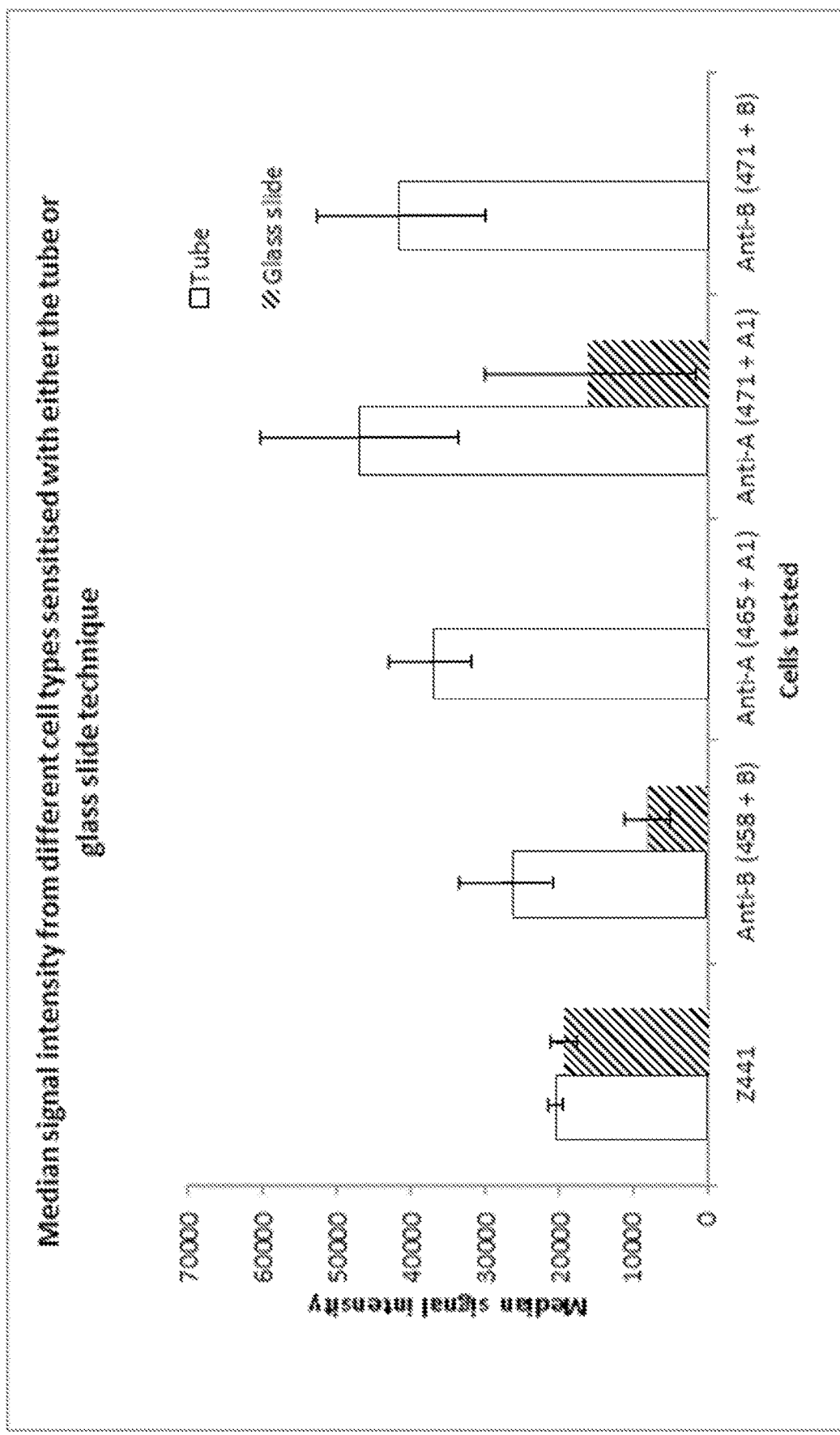

FIGS. 8 *a* & *b*: Images of slides CM62 and CM63 showing the results for Anti-A and Anti-B plasmas tested with $A_1$ or B cells using the tube or glass slide techniques respectively. Also shown are the results for the indirect test using AHG in tubes with the agglutination grading result down the left hand side of the figure. Note that this testing was performed manually and, therefore, some disruption may be evident that would be reduced/eliminated when automated methods are employed.

Figure 9:
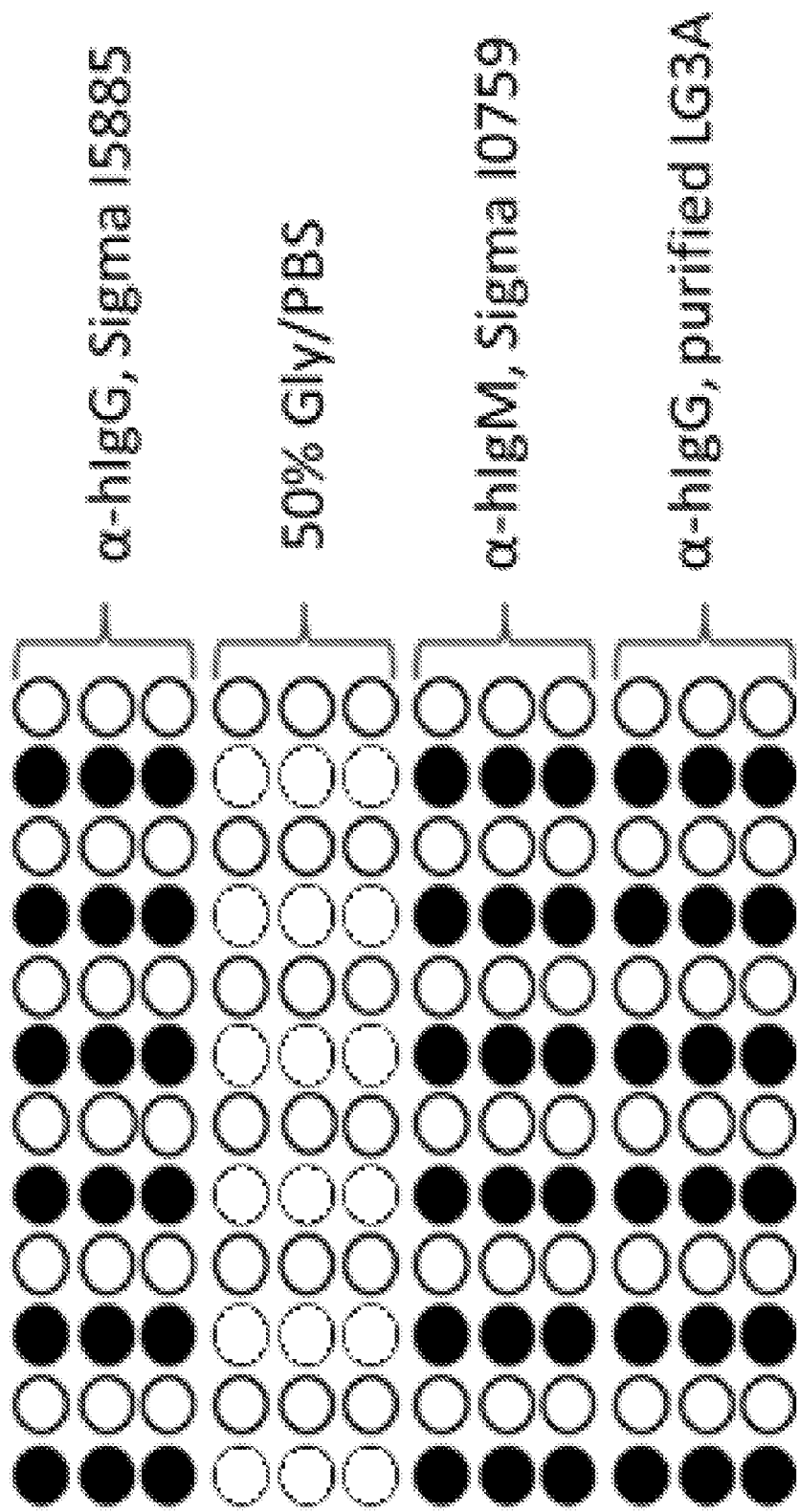

FIG. 9: Diagrammatic representation of a single array showing the antibodies printed. Anti-human IgM was printed at 518 μg/mL and α-hIgG at 301 μg/mL. 16 arrays were printed on each slide in a 2×8 format. Black spots indicate a positive cell binding response and white spots indicate 50% glycerol/PBS printed as negative spots which should not bind any cells.

Figure 10:
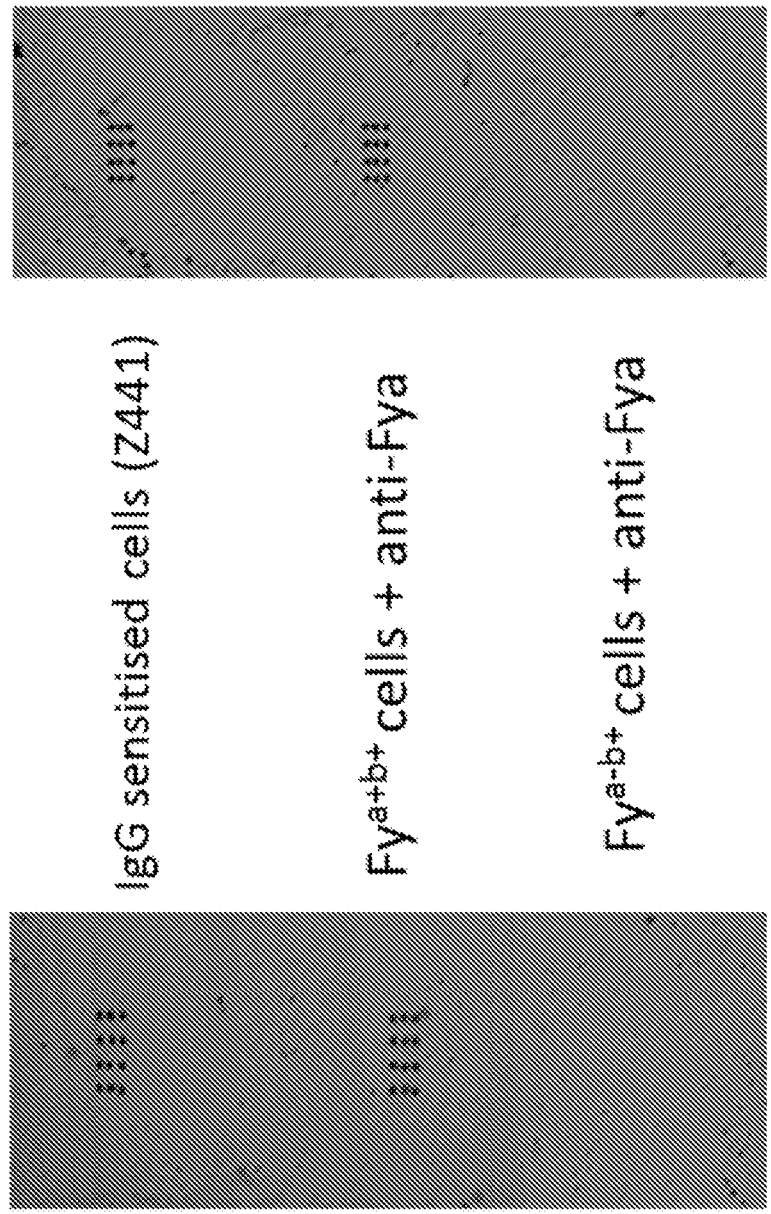

FIG. 10: Image of slides 1 and 2 showing the results for Fy(a+b+), Fy(a+b−) and Fy(a−b+) cells sensitised with monoclonal anti-$Fy^a$ for 30 minutes using the tube or glass slide technique. Also shown are the results for the positive control cells (IgG Sensitised Cells, Z441).

Figure 11:
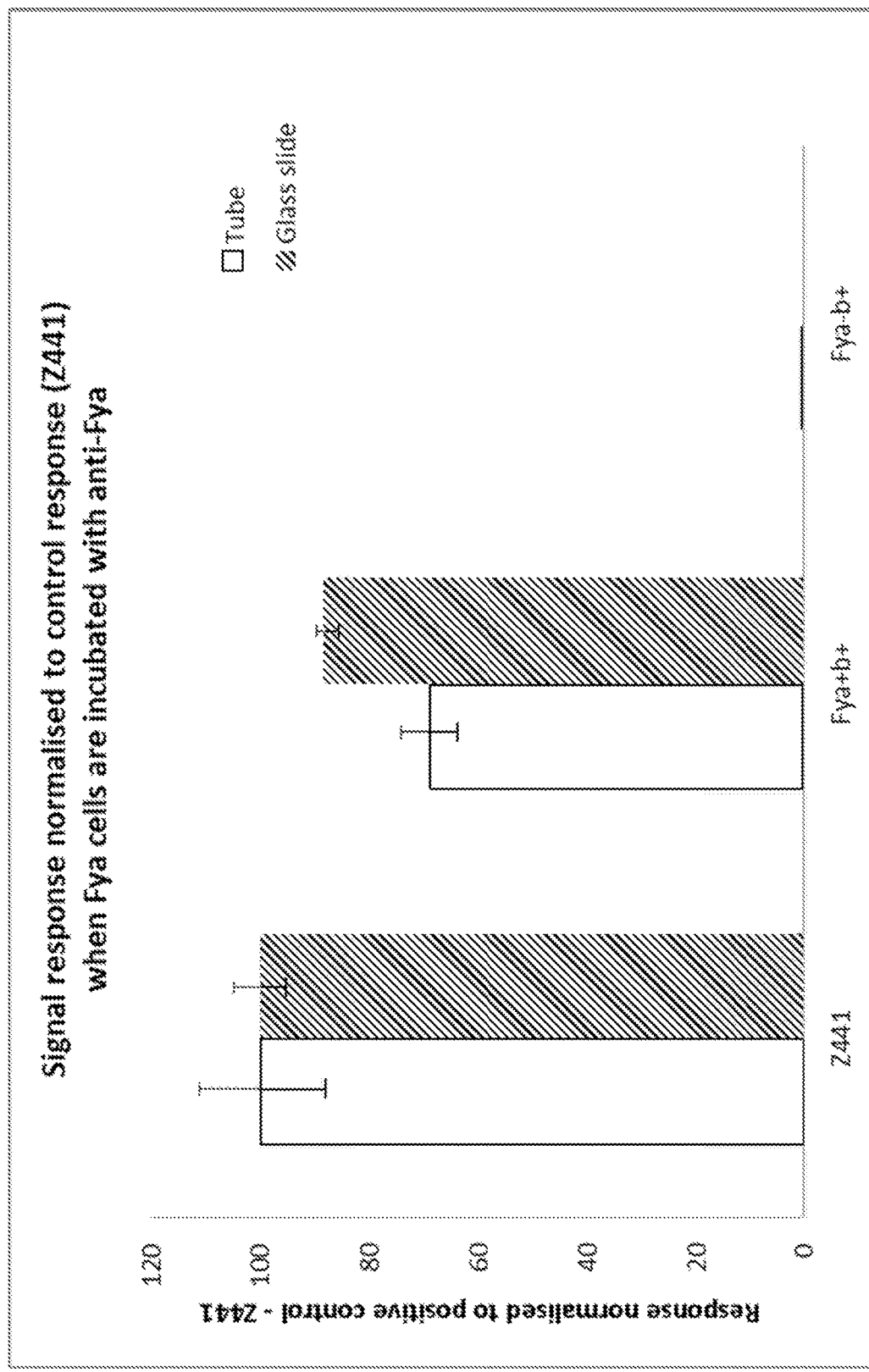

FIG. 11: Data generated from images shown in FIG. 11, showing the signal response which has been normalized to the median signal intensity for the positive control cells (Z441) tested on the slide. Because the results for the tube and slide technique were performed on separate slides, this accounts for any differences in signal across arrays on different slides. The results for the tube or glass slide technique are shown. The IgG sensitised cells (Z441) demonstrate the control signals. When using the monoclonal Anti-$Fy^a$, good binding is seen by both techniques. The Fy(a−b+) cell shows low or negative reactivity as expected. In this way we can see that the sample containing Anti-$Fy^a$ is incompatible with Fy(a+) cells and negative with Fy(a−), demonstrating the principle of the crossmatch.

Example 1—Preparation of Protein Microarrays

Coated slides obtained from Schott were used as the substrate. The binding agent antibody probe samples to be spotted were prepared in 50% Glycerol/50% PBS.

The slides were printed using an Arrayjet Sprint Arrayer (Arrayjet) with a 12 sample Jetspyder. Replicates of each sample were printed on each slide separated by negative control spots of 50% glycerol/PBS—see FIG. 3. All slides were printed within a relative humidity between 40-60%, and at an ambient temperature (20-23° C.), Printed probes were left to immobilise in the humidified atmosphere for 30 minutes prior to being stored in a box at 2-8° C. in the dark for at least 24 hours. Further arrays were printed for the testing of anti-A and anti-B plasmas which are shown in FIG. 4.

Example 2—Washing of Cells Prior to Use in Experiments

All cell types were suspended in LISS or washed into LISS (low ionic strength saline)—other diluents may be used, including, for example PBS, Modified Alsevers, and variations thereof. Moreover, cells need not be washed—rather a small volume of cells may be removed from the donor sample (which has perhaps been centrifuged) directly into LISS buffer. Where washing was used, cells were centrifuged three times at 3000 rpm for 2 minutes using a Thermo Centra CL2 centrifuge with the supernatant removed each time and replaced with ~4 mL PBS. After the final centrifugation, one wash in LISS was performed before re-suspending the cells to 2% HCT in LISS.

For some experiments where different haematocrits of cells were tested cells were prepared at 8% HCT (160 μL of the resultant cell pellet was added to 1000 μL of LISS). The 8% HCT cells were then diluted further in LISS to achieve the required percentage haematocrit.

Example 3—Indirect Agglutination Testing of Sensitised Cells (Conventional Method, Reference Technique)

Volumes (40 μL or 80 μL) of the cell suspension were incubated with 80 μL of neat or diluted plasma in a tube. The resulting mix was incubated in a water bath at 37° C. In this example, the mix was incubated for 30 or 45 minutes but shorter or longer times could be used. Under these conditions, the red blood cells are sensitised. Where plasma was diluted, the diluent may be the same as that used for the red cells suspension—other suitable diluents can be used.

Following the incubation period, cells were washed using the nW program on a DiaCent 2000 Cell washer (×4 washes with PBS, then centrifugation at 1000 g). Two drops of AHG were added and the tubes were finally centrifuged (1000 g, 10 secs) and agglutination of cells read over a light box.

Example 4—Tube Technique for Sensitising Cells

Volumes (240 μL—or matched with volume of plasma) of cell suspension was incubated with 480 μL neat or diluted plasma. Plasma was diluted in either PBS or LISS. Tubes were incubated at 37° C. (for 30 or 45 minutes—longer or shorter times may be used). Following the incubation period, cells were washed using a DiaCent 2000 Cell washer (×4 washes with PBS and a final centrifugation). Cells were then resuspended in 240 μL 2% BSA/LISS prior to adding to the arrays as described in Example 7.

Example 5—Glass Slide Technique for Sensitising Cells (Removal of Unbound Antibody by Removing Plasma/Supernatant and Resuspension)

A blank slide (Schott, Glass B) was fitted into a Grace-Bio 16-well manifold. Blocking solution (2% BSA/PBS) was warmed to approximately 37° C. and slides were blocked by addition of 160 μL of blocking solution to each well and incubated at 37° C. with shaking (350 rpm) on a Grant Bio Thermoshaker for 15 minutes (with plastic cover). After blocking the solution was removed and 80 μL of (optionally washed) cells were incubated with 160 μL plasma. The slide was incubated stationary for 30 or 45 minutes at 37° C. Incubation time was dependent on the experiment being performed.

Following the incubation (substantially) the whole volume of liquid (or liquid phase) was removed quickly from the top right hand corner of each well.

The remaining cells were re-suspended in 240 μL 2% BSA/LISS prior to adding to the arrays as described in Example 7.

Example 6—Plate Technique for Sensitising Cells (Removal of Sensitised Erythrocytes from Plasma/Supernatant and then Resuspension)

Volumes (40 μL) of washed cells were incubated with 80 μL plasma stationary in a U-bottomed 96 well plate for 30 or 45 minutes at 37° C. using a Grant Bio Thermoshaker. For investigating the change in total volume, 80 μL of cells were incubated with 160 μL plasma. Incubation time was dependent on the experiment being performed. Following the incubation time 4 μL of the cell pellet from the bottom of the well was removed to a separate well containing 100 μL 2% BSA/LISS. The cells were re-suspended prior to adding to the arrays as described in Example 7.

Example 7—Processing of Arrays

Printed array slides were removed from 2-8° C. storage and fitted into Grace-Bio 16-well manifolds ensuring both central and straight alignment of the arrays in each well, secured using the metal clips and fitted into a Proplate tray (3 slide type). Slides were returned to storage at 2-8° C. until immediately prior to use. Blocking solution (2% BSA/PBS) was warmed to approx. 37° C. Slides were blocked by adding 160 μL of blocking solution to each well and incubated at 37° C. with shaking at 350 rpm on a Grant Bio PHMP Thermoshaker for 15 minutes (with plastic cover).

After blocking the solution was removed and 120 μL of sensitised cells (from Examples 4-6) were slowly pipetted into the left hand side of each appropriate well.

Slides were incubated stationary at 37° C. for 15 minutes (with plastic cover). Following incubation, the whole Proplate tray containing slides was dipped into a tub of PBS. Suction may be used to remove the PBS and any other fluid in the wells.

Slides were carefully removed from the Grace-Bio manifold and transferred to a slide holder and submerged into fresh PBS. Optionally slides may be fixed by immersion in 0.1% gluteraldehyde/PBS for 10 minutes at 2-8° C., or more conveniently the PBS is removed by suction and analysis performed directly using the flatbed scanner. This was followed by a final wash in water before centrifuged to dryness. Slides stored in a dust-free dark place until scanning.

Example 8—Data Extraction and Analysis

Slides were scanned using a flatbed scanner to capture a high resolution image and saved as a 16-bit TIFF file.

Where red blood cells are bound to antibodies a black spot is evident.

Numerical data was extracted from the microarrays using an in-house generated algorithm that can quantify the signal intensity.

A text input file was self-generated using microarray column and row positions to determine identity and location of each probe. This was used to generate an array list that was loaded once the microarray grid settings had been set up. Once the grid and the array list had been generated, the data was extracted to a text file. This process gave the median fluorescence intensity value from the centre of each spot and a median background value from the entire background area of the slide. This information was collected into an Excel worksheet.

For each spot the background value was subtracted from the spot intensity value. For each slide the signal intensity values from each different scan setting were collated into one worksheet.

Once the best data scan had been selected it was processed as follows. Unwanted data were removed from the worksheet to leave only one value per spot on the microarray (the spot intensity value minus the background value for each spot). The negative control values were used to calculate a 'noise' value—the mean plus two standard deviations of the negatives (mean+2 sd). This value represents non-specific binding (NSB). The value for each spot was divided by the mean+2 sd of the negative controls to give a signal-to-noise ratio (S/N). Values over one can be considered significant. The median of the S/N was calculated for the replicate spots of each sample.

Using Microsoft Excel the processed data was analysed as appropriate. Bar charts were used throughout to analyse data. The Y-axis on the bar charts represents the S/N median for the sample.

Where error bars were included, the standard error for each sample was calculated as follows. The standard deviation of the replicates of each sample was calculated (this was performed on S/N ratios or actual values). The standard deviation was divided by the square root of the number of replicates of the sample to give the standard error.

Supplementary Data

Protein Microarrays were prepared as per Example 1 above. Cells were washed prior to experiments as per Example 2 above. Indirect agglutination testing of sensitised cells (conventional method: reference technique) was performed as per Example 3 above. The "tube technique" for preparing sensitised cells was performed as per Example 4 above. The "glass slide technique" for sensitising cells (removal of unbound antibody (without centrifugation/washing) by removing plasma/supernatant and re-suspension) was performed as per Example 5 above. Assays were processed as per Example 7 above.

Data Extraction and Analysis

As per Example 8 of original patent except that the Y-axis on the bar charts represents the S/N median for the sample normalised to the positive control (Z441) result and calculated as a percentage.

Where error bars were included, the % Coefficient of Variance associated with the value for each sample was calculated as follows. The % CV of the replicates of each sample was calculated (this was performed on S/N ratios or actual values). The mean value was standard deviation and then multiplied by 100 to give the % CV.

REFERENCES

Robb. J. S., Roy, D. J., Ghazal, P., Allan, J. and Petrik, J. (2006). "Development of non-agglutination microarray blood grouping" Transfusion Medicine. 16, 119-129.

Campbell, C. J., O'Looney, N., Chong Kwan, M., Robb, J. S., Ross, A. J., Beattie, J. S., Petrik, J. and Ghazal, P. (2006). "Cell Interaction Microarray for Blood Phenotyping" Analytical Chemistry. 78, 1930-1938.

British Committee for Standards in Haematology; Milkins, C., et al. (2013). Guidelines for pre-transfusion compatibility procedures in blood transfusion laboratories. Transfusion Medicine 23, 3-35.

Issit, P. D. and Anstee, D. J. (1998) Applied Blood Group Serology. Fourth Edition. Montgomery Scientific Publications.

The invention claimed is:

1. A method of detecting red blood cells in a sample, said method comprising contacting the sample with binding agents capable of binding the red blood cell antigens control method for an assay, which assay requires the addition of red blood cells, said control method comprising:
   detecting red blood cells with binding agents capable of binding red blood cells antigens listed as (i)-(iv) and that have a frequency of at least 99% in all red blood cell types:
   (i) GPA;
   (ii) GPB;
   (iii) H; and
   (iv) Rh29; and
   confirming the presence of the red blood Cells in the assay and continuing the assay or confirming the absence of the red blood cells in the assay and discarding the assay or repeating the assay,
      wherein detection of red blood cells bound to the binding agents confirms the presence of red blood cells in the sample.

2. The method of claim 1, wherein the method is a control test to confirm the presence of red blood cells in a sample or process.

3. The method of claim 1, wherein the sample is a sample of whole blood or a sample of adult, foetal, neonatal and/or antenatal plasma, serum or red blood cells prepared therefrom.

4. The method of claim 1, wherein the sample is any volume or amount of a fluid or substance which comprises, potentially comprises or is suspected of comprising, red blood cells.

5. The method of claim 1, wherein the method is a control test for an assay.

6. The method of claim 1, wherein the binding agents are selected from the group consisting of:
   (i) antibody or an antigen binding fragment thereof,
   (ii) aptamers,
   (iii) small molecule antibody mimetics,
   (iv) nucleic acid ligands, and
   (v) receptors from cells capable of binding the red blood cell antigens.

7. The method of claim 1, wherein the binding agents are an antibody or an antigen binding fragment thereof.

8. The method of claim 1, wherein the binding agents are an antibody, optionally a polyclonal or monoclonal antibody or antigen binding fragment of either.

9. The method of claim 1, wherein the binding agents are immobilised, bound or adsorbed on to any suitable substrate.

10. The method of claim 1, wherein the binding agents are immobilised, bound or adsorbed to all or part of a substrate.

11. The method of claim 1, wherein the binding agents are immobilised, bound or adsorbed to one or more discrete, predetermined locations on a substrate.

12. The method of claim 11, wherein the binding agents are immobilised as a plurality/series of distinct and/or discrete spots.

13. The method of claim 11, wherein each discrete or predetermined location or spot on a substrate independently comprises the immobilised binding agents.

14. The method of claim 13, wherein the binding agents are is immobilised, bound, and/or adsorbed to a substrate as an array or microarray.

15. The method of claim 1, wherein the binding agents are immobilised to the substrate of an existing assay system.

16. The method of claim 15, wherein, the existing assay system is a crossmatching or blood typing assay system.

17. The method of claim 9, wherein the substrate is functionalised with one or more functional polymers selected from the group consisting of:
   (i) glycidoxypropyltriethoxysilane;
   (ii) poly-1-lysine;
   (iii) aminopropylsilane;
   (iv) carboyxsilane;
   (v) hydrogels and polymer-brushes;
   (vi) self-assembled monolayers; and
   (vii) a silane based coating.

18. The method of claim 1 wherein the red blood cells are detected by means of autofluorescence.

19. A method, of confirming the presence of red blood cells in a sample used in an assay, said method comprising contacting the sample with one or more binding agents capable of binding red blood cells antigens (i)-(iv) that have a frequency of at least 99% in all red blood cell types selected from the group consisting of:
   (i) GPA;
   (ii) GPB;
   (iii) H; and
   (iv) Rh29;
   wherein the detection of red blood cells bound to the binding agents confirms the presence of red blood cells in the sample and further wherein the assay is selected from the group consisting of:
   (i) an immunological assay;
   (ii) a crossmatching assay; and
   (iii) a blood typing assay.

20. The method of claim 19, wherein the method further comprises contacting the sample with binding agents capable of binding one or more red blood cell antigens selected from the group consisting of:
   (i) $En^a$;
   (ii) Ge:2;
   (iii) Ge:3; and
   (iv) $Wr^b$.

21. A control test for an assay, said test comprising monoclonal antibodies capable of binding the red blood, cell antigens (i)-(iv) that have a frequency of at least 99% in all red blood cell types:
   (i) GPA;
   (ii) GPB;
   (iii) H; and
   (iv) Rh29.

22. The control test of claim 21, wherein the test further comprises one or more binding agents capable of binding one or more of the red blood cell antigens selected from the group consisting of:
   (I) $En^a$;
   (ii) Ge:2;
   (iii) Ge:3; and
   (iv) $Wr^b$.

23. The control test of claim 21, wherein the control test is used as a positive control test to confirm the addition of red blood cells to a process, device, apparatus, assay and/or assay system.

24. The method of claim 1, wherein the method further comprises contacting the sample with binding agents capable of binding one or more red blood cell antigens selected from the group consisting of:
   (i) $En^a$;
   (ii) Ge:2;
   (iii) Ge:3; and
   (iv) $Wr^b$.

* * * * *

UNITED STATES PATENT AND TRADEMARK OFFICE
CERTIFICATE OF CORRECTION

PATENT NO. : 10,613,102 B2
APPLICATION NO. : 15/119291
DATED : April 7, 2020
INVENTOR(S) : Robb et al.

Page 1 of 1

It is certified that error appears in the above-identified patent and that said Letters Patent is hereby corrected as shown below:

In the Claims

Column 32, Lines 9-11, Claim 1:
Please delete the phrase "method of detecting red blood cells in a sample, said method comprising contacting the sample with binding agents capable of binding the red blood cell antigens"

Column 32, Line 22, Claim 1:
Please correct "Cells" to read -- cells --

Column 33, Lines 1-2, Claim 14:
Please correct "agents are is immobilized" to read -- agents are immobilized --

Column 33, Line 14, Claim 17:
Please correct "carboyxsilane" to read -- carboxysilane --

Column 33, Line 21, Claim 19:
Please correct "method, of" to read -- method of --

Column 33, Line 25, Claim 19:
Please delete the phrase "selected from the group consisting of:"

Column 34, Line 20, Claim 22:
Please correct "(I)" to read -- (i) --

Signed and Sealed this
Second Day of June, 2020

Andrei Iancu
*Director of the United States Patent and Trademark Office*